US009909989B2

United States Patent
Chou et al.

(10) Patent No.: US 9,909,989 B2
(45) Date of Patent: *Mar. 6, 2018

(54) STRUCTURES FOR ENHANCEMENT OF LOCAL ELECTRIC FIELD, LIGHT ABSORPTION, LIGHT RADIATION, MATERIAL DETECTION AND METHODS FOR MAKING AND USING OF THE SAME

(71) Applicant: The Trustees of Princeton University, Princeton, NJ (US)

(72) Inventors: Stephen Y. Chou, Princeton, NJ (US); Wendi Li, Mountain View, CA (US)

(73) Assignee: The Trustees of Princeton University, Princeton, NJ (US)

( * ) Notice: Subject to any disclaimer, the term of this patent is extended or adjusted under 35 U.S.C. 154(b) by 207 days.

This patent is subject to a terminal disclaimer.

(21) Appl. No.: 14/871,678

(22) Filed: Sep. 30, 2015

(65) Prior Publication Data

US 2016/0258867 A1 Sep. 8, 2016

Related U.S. Application Data

(62) Division of application No. 13/699,270, filed as application No. PCT/US2011/037455 on May 20, 2011, now Pat. No. 9,182,338.

(Continued)

(51) Int. Cl.
*G01J 3/00* (2006.01)
*G01N 21/64* (2006.01)
(Continued)

(52) U.S. Cl.
CPC .............. *G01N 21/64* (2013.01); *B82Y 15/00* (2013.01); *B82Y 30/00* (2013.01); *G01N 21/03* (2013.01);
(Continued)

(58) Field of Classification Search
CPC ........ B82Y 15/00; B82Y 30/00; G01N 21/64; G01N 21/648; G01N 2021/0378;
(Continued)

(56) References Cited

U.S. PATENT DOCUMENTS 5,552,272 A 9/1996 Bogart
5,866,430 A 2/1999 Grow
(Continued)

FOREIGN PATENT DOCUMENTS

JP 2007319988 12/2007
WO WO2006138442 12/2006
(Continued)

OTHER PUBLICATIONS

Hu, et al., "Effects of nanodots on surface plasmons and electric field enhancement in nano-pillar antenna array", Quantum Electronics and Laser Science Conference, San Jose, California, US, May 16-21, 2010.
(Continued)

*Primary Examiner* — Tri Ton
*Assistant Examiner* — Rufus Phillips
(74) *Attorney, Agent, or Firm* — James S. Keddie; Bozicevic, Field & Francis, LLP

(57) ABSTRACT

Microstructures and nanostructures (100) consisting of a substrate (110), an array of pillars (120) capped by metallic disc (130), metallic dots (clusters or granules) (140) disposed on the sidewalls of the pillars, and a metallic backplane (150) that can interact to enhance a local electric field, the absorption of the light, and the radiation of the light are disclosed. Methods to fabricate the structures (100) are also disclosed. Applications of the structures to enhance the optical signals in the detection of molecules and other
(Continued)

materials on a structure surface, such as fluorescence, photoluminescence and surface enhanced Raman Scattering (SERS) are also disclosed.

20 Claims, 20 Drawing Sheets

Related U.S. Application Data

(60) Provisional application No. 61/347,178, filed on May 21, 2010.

(51) Int. Cl.
    *G01N 21/65*      (2006.01)
    *B82Y 15/00*      (2011.01)
    *G01N 21/552*      (2014.01)
    *G01N 21/59*      (2006.01)
    *B82Y 30/00*      (2011.01)
    *G01N 21/03*      (2006.01)

(52) U.S. Cl.
CPC .......... *G01N 21/554* (2013.01); *G01N 21/59* (2013.01); *G01N 21/648* (2013.01); *G01N 21/6452* (2013.01); *G01N 21/658* (2013.01); *G01N 2021/0378* (2013.01); *G01N 2021/6482* (2013.01); *Y10T 428/24174* (2015.01)

(58) Field of Classification Search
CPC .......... G01N 2021/6482; G01N 21/03; G01N 21/554; G01N 21/59; G01N 21/6452; G01N 21/658; G01N 21/6486; Y10T 428/24174

See application file for complete search history.

(56) References Cited

U.S. PATENT DOCUMENTS

| | | |
|---|---|---|
| 6,743,581 B1 | 6/2004 | Vo-Dinh |
| 7,153,682 B2 | 12/2006 | Charych et al. |
| 7,245,370 B2 | 7/2007 | Bratkovski et al. |
| 7,426,025 B2 | 9/2008 | Wang |
| 7,586,601 B2 | 9/2009 | Ebstein |
| 7,713,849 B2 | 5/2010 | Habib et al. |
| 7,714,317 B2 | 5/2010 | Suiter et al. |
| 7,851,172 B2 | 12/2010 | Lovell et al. |
| 2002/0109110 A1 | 8/2002 | Some et al. |
| 2004/0156108 A1 | 8/2004 | Chou et al. |
| 2006/0034729 A1 | 2/2006 | Poponin |
| 2007/0155021 A1 | 7/2007 | Zhang et al. |
| 2008/0145964 A1 | 6/2008 | Linden |
| 2009/0097022 A1 | 4/2009 | Shen et al. |
| 2009/0149344 A1 | 6/2009 | Zhao et al. |
| 2010/0078855 A1 | 4/2010 | Chou et al. |
| 2011/0128536 A1 | 6/2011 | Bond et al. |
| 2011/0166045 A1 | 7/2011 | Dhawan et al. |

FOREIGN PATENT DOCUMENTS

| | | |
|---|---|---|
| WO | WO2007/004390 | 1/2007 |
| WO | WO2011016057 | 9/2011 |
| WO | WO2012024006 | 2/2012 |
| WO | WO2014055559 | 4/2014 |

OTHER PUBLICATIONS

Li, et al. "Three-dimensional cavity nanoantenna coupled plasmonic nanodots for ultrahigh and uniform surface-enhanced Raman scattering over large area", Feb. 2011, Optics Express, vol. 19, No. 5, pp. 3925-3936.
Love, et al. Self-Assembled Monolayers of Thiolates on Metals as a Form of Nanotechnology Chern. Rev. 2005, 105, pp. 1103-1169.
Su, K-H., et al. "Interparticle coupling effects on plasmon resonances of nanogold particles." Nano Letters 3.8 (2003): 1087-1090.
Zhang, et al., "Giant and uniform fluorescence enhancement over large areas using plasmonic nanodots in 3D resonant cavity nanoantenna by nanoimprinting", May 2012, Nanotechnology, vol. 23, pp. 1-9.
Zhou, et al., "Enhancement of Immunoassay's Fluorescence and Detection Sensitivity Using Three-Dimensional Plasmonic Nano-Antenna-Dots Array", Apr. 2012, ACS Publications, vol. 84, pp. 4489-4495.

(1.)
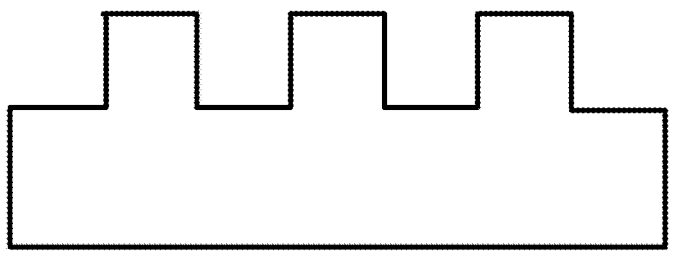
(2.)
FIG. 5B
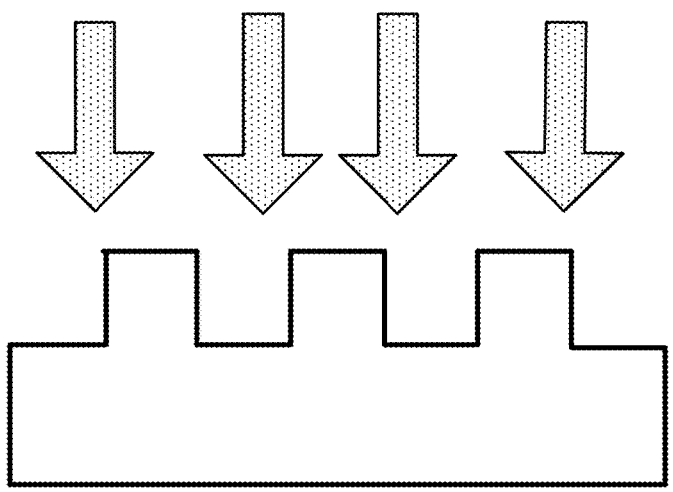
(3.)
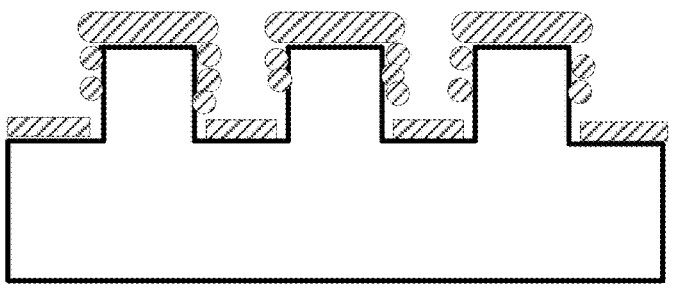
(4.)

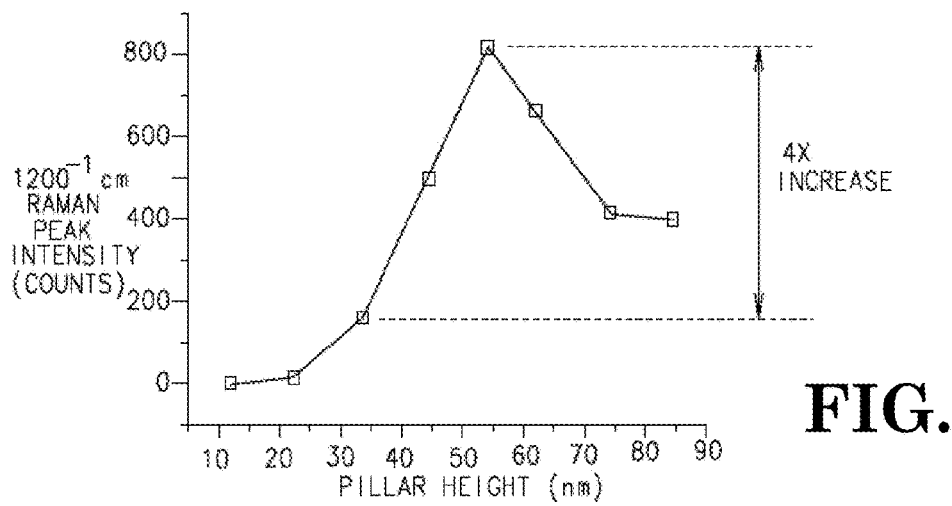
FIG. 7B
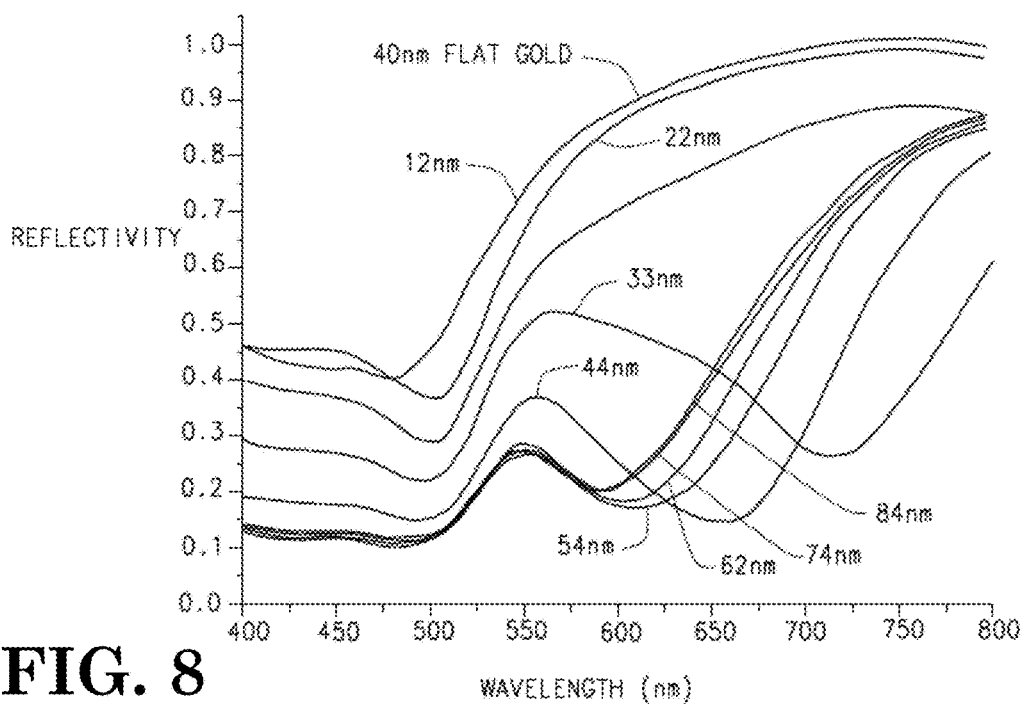
FIG. 8
(A) (B) (C) (D) (E) (F) (G) (H)

FIGURE 9
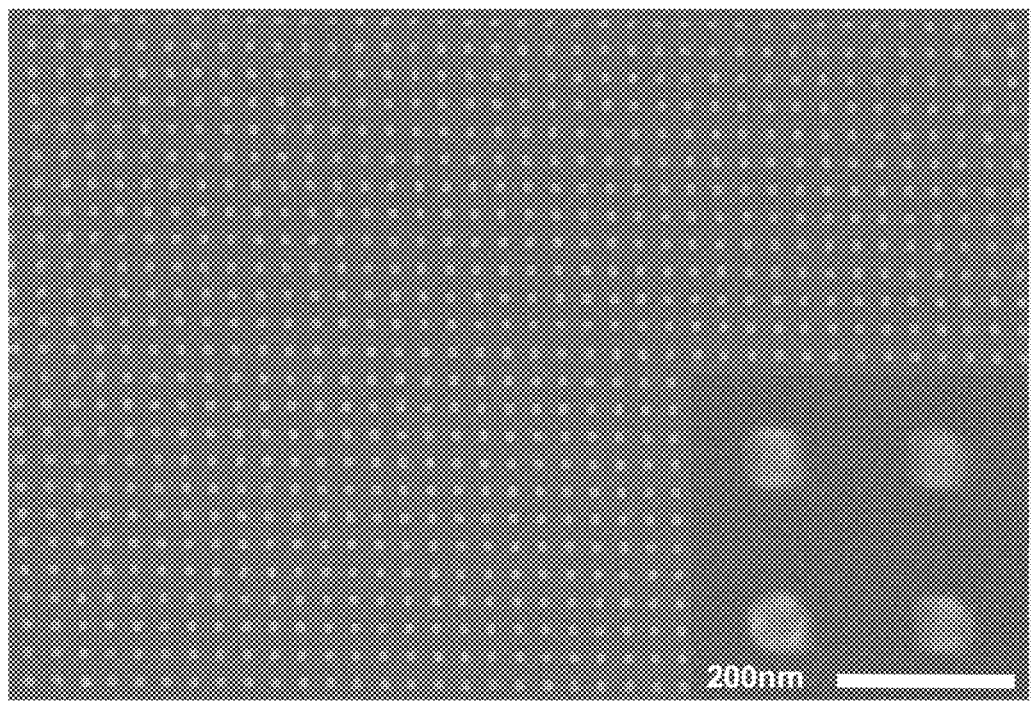
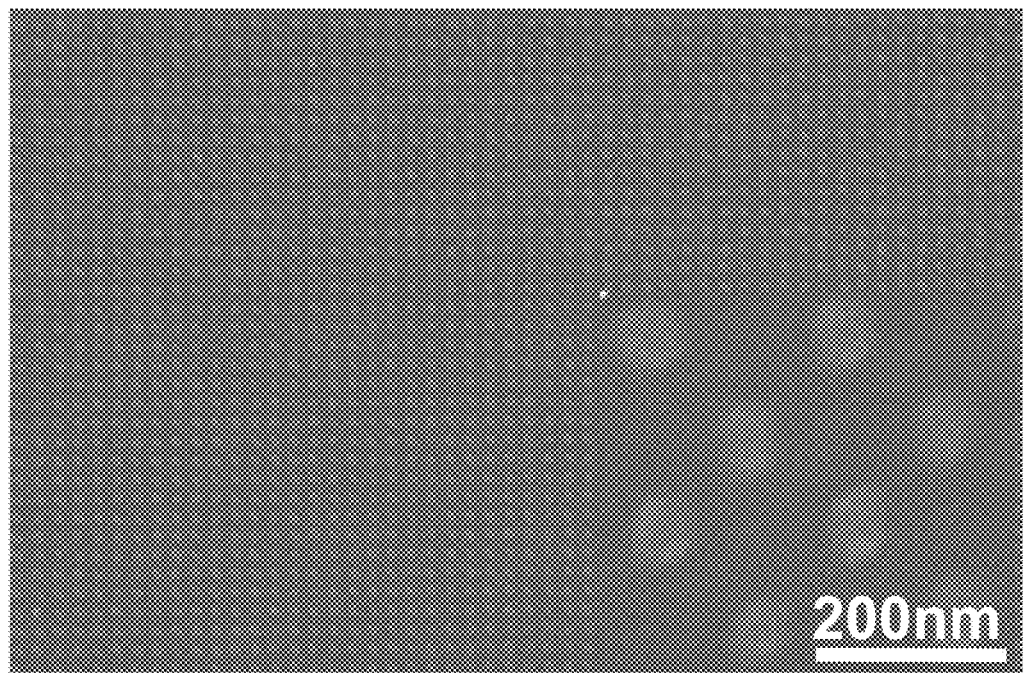
FIGURE 10

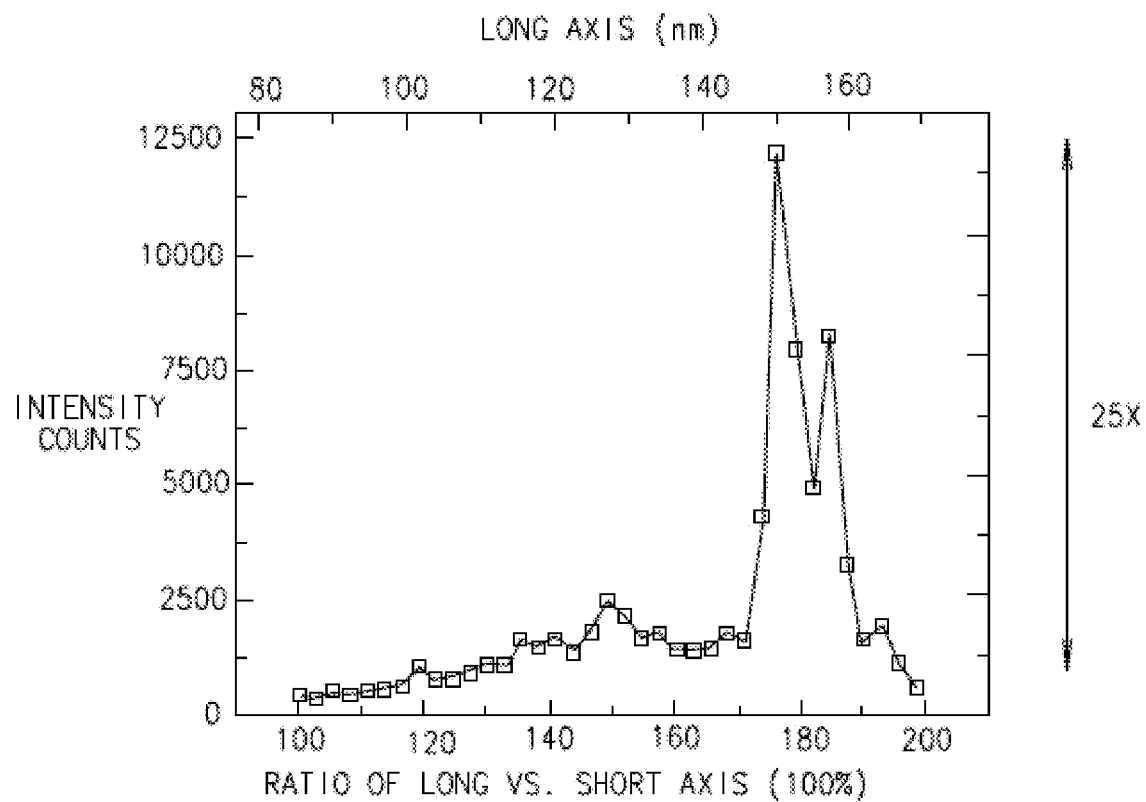
FIGURE 14
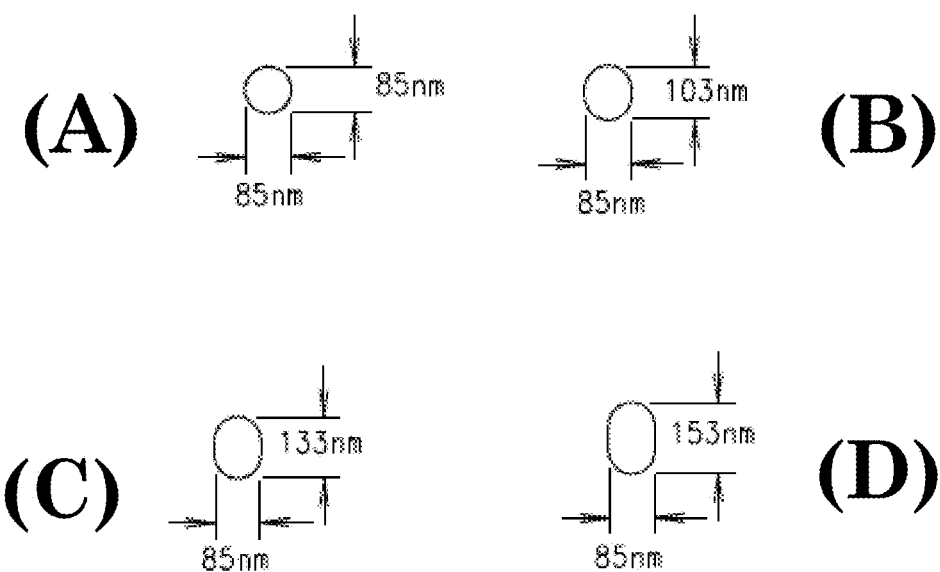

(A)      (B)      (C)

STRUCTURES FOR ENHANCEMENT OF LOCAL ELECTRIC FIELD, LIGHT ABSORPTION, LIGHT RADIATION, MATERIAL DETECTION AND METHODS FOR MAKING AND USING OF THE SAME

CROSS-REFERENCE TO RELATED APPLICATIONS

The present application is related to, and claims priority from, U.S. Provisional Patent Application Ser. No. 61/347,178 to Chou et al. for "Structures For Enhancement Of Local Electric Field, Light Absorption, And Light Radiation, And The Making Of The Same" filed on May 21, 2010, which is herein incorporated by reference.

STATEMENT REGARDING FEDERALLY SPONSORED RESEARCH

This invention was made with United States government support under Grant No. FA9550-08-1-0222 awarded by the Air Force Office of Scientific Research. The United States government has certain rights in this invention.

BACKGROUND OF THE INVENTION

The application is related to the microscale and nanoscale structures for achieving an enhancement of properties of the structure or the materials, including a molecule placed on or near the structure, their fabrication, and the application of such structures and enhanced materials. The properties include physical, chemical, or biological properties. The physical properties may include optical and electrical properties.

The enhanced properties can be very useful for detection of a material or enhancing the performance of electrical and optical devices, which include solar cells, lasers, light-emitting diodes, and displays. For example, there is a great need to develop microscale and nanoscale structures that enhance the local electric field, the absorption of the light, and the radiation of the light of a material, which in turn can be utilized to enhance optical signals employed in the detection of molecules and other materials on a structure surface, such as fluorescence, photoluminescence, and Surface Enhanced Raman Scattering (SERS).

BRIEF SUMMARY OF THE INVENTION

Briefly stated, the present disclosure provides microstructures and nanostructures for a material that can enhance the local electric field induced in the material by incoming light, the absorption of light by the material, and the radiation of light generated at a surface of the material. Methods to fabricate the structures are also disclosed. Applications of the structures to enhance optical signals in the detection of molecules and other materials on a structure surface, such as fluorescence, photoluminescence, and Surface Enhanced Raman Scattering (SERS) are also disclosed.

The foregoing features, and advantages set forth in the present disclosure as well as presently preferred embodiments will become more apparent from the reading of the following description in connection with the accompanying drawings.

BRIEF DESCRIPTION OF THE SEVERAL VIEWS OF THE DRAWINGS

In the accompanying drawings which form part of the specification:

FIG. 5B shows an alternate exemplary fabrication process for making Disc-Coupled Dots-on-Pillar Antenna Array (D2PA);

FIG. 7B charts the effects of the Pillar Height on Raman peak intensity (counts);

FIG. 8 shows a graph of the measured effects on the NPA $SiO_2$ Pillar Height on the measured Light Reflectivity (Absorption) for a variety of pillar heights, shown in the scanning electron micrographs (A)-(H) (pillar height: 12, 22, 33, 44, 54, 62, 74, and 84 nm);

FIG. 9 shows a scanning electron micrograph of an array of Single Pillars Per Unit Cell (with the pillar period of 200 nm) fabricated by nanoimprint;

FIG. 10 shows a scanning electron micrograph of an array of Double Pillar Per Unit Cell (with the pillar period of 200 nm) fabricated by nanoimprint;

FIG. 14 shows a measured D2PA Nano-Pillar shape effect on SERS EF for pillar shapes shown in (A)-(D);

Corresponding reference numerals indicate corresponding parts throughout the several figures of the drawings. It is to be understood that the drawings are for illustrating the concepts set forth in the present disclosure and are not to scale.

Figure 1A:
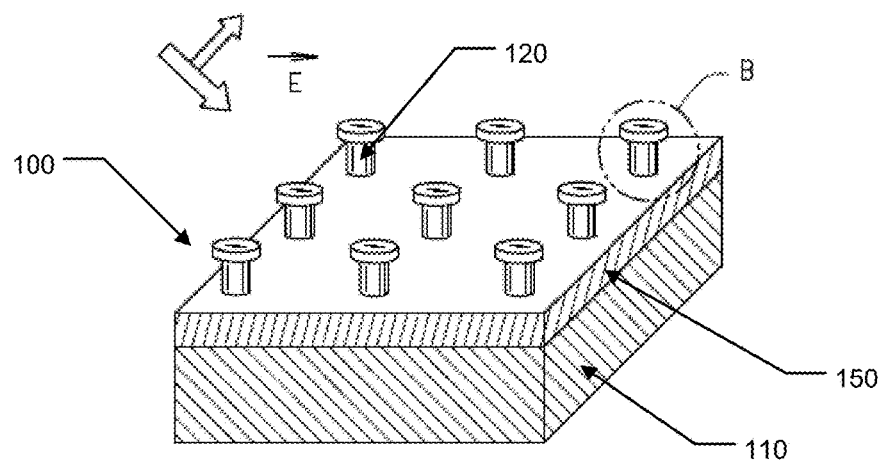
FIG. 1A shows an example structure of Disc-Coupled Dots-on-Pillar Antenna-Array (D2PA), consisting of dense 3D cavity nanoantennas in the form of a $SiO_2$ pillar array with a metal disc on top of each pillar, a metal backplane on the foot of the $SiO_2$ pillars, and metallic nanodots on the $SiO_2$ pillar sidewalls, all coupled through nanogaps.

Before any embodiments of the invention are explained in detail, it is to be understood that the invention is not limited in its application to the details of construction and the arrangement of components set forth in the following description or illustrated in the drawings.

DETAILED DESCRIPTION

The following detailed description illustrates the invention by way of example and not by way of limitation. The description enables one skilled in the art to make and use the present disclosure, and describes several embodiments, adaptations, variations, alternatives, and uses of the present disclosure, including what is presently believed to be the best mode of carrying out the present disclosure.

Disclosed are microstructures and nanostructures that can enhance the local electric field, enhance the absorption of the light, and enhance the radiation of the light, from a material which in turn can enhance the optical signals utilized in the detections of molecules and other materials on a structure surface, such as fluorescence, photoluminescence and Surface Enhanced Raman Scattering (SERS).

The microstructures and nanostructures, termed "3-dimensional antenna coupled nanoscale plasmon structures" (3DANPS), have a 3D antenna (of a dimension that absorbs the light wavelength of interest) that is coupled to nanoscale plasmon (metallic) nanostructures to enhance the local electric field as well as enhance the light absorption and the light radiation.

Figure 1B:
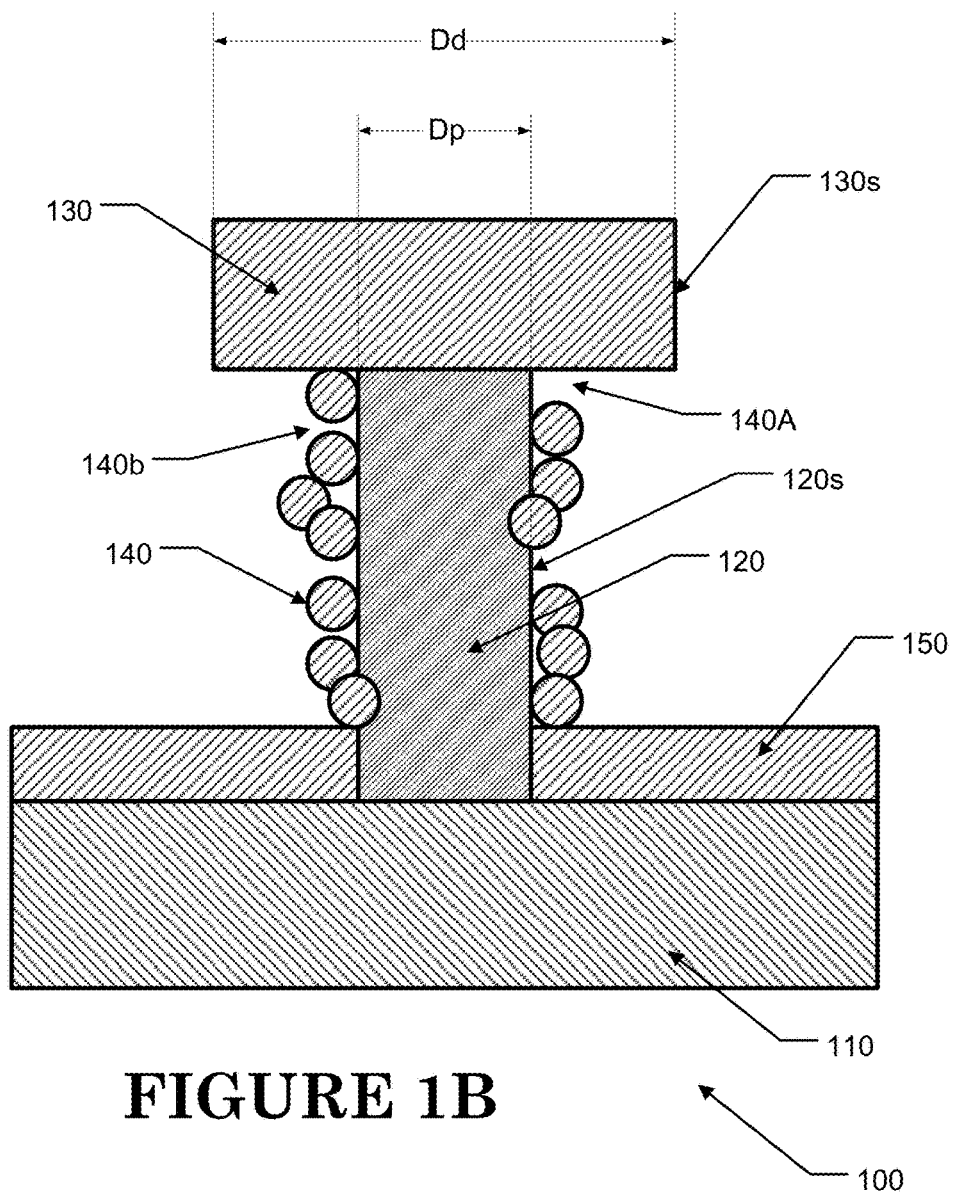
FIG. 1B is a cross-sectional view of a pillar of FIG. 1A.

One embodiment of a 3DANPS is termed "Disc-coupled dots-an-pillar antenna array" (D2PA) and is shown at 100 in FIGS. 1A and 1B. The D2PA has a 3D plasmon cavity antenna with a floating metallic disc or nanodisc (130) that is coupled to nanoscale metallic dots on a pillar (120). Specifically, the D2PA has a substrate (110), a pillar array (120) on the substrate, a metallic disc or nanodisc (130) on top of each of the pillars, nanoscale metallic dots (140) on the pillar sidewall, with gaps between the disc and some of the dots, gaps between the neighboring dots, and a metallic back-plane (150) which covers the most of the substrate areas that are not occupied by the pillars.

In one embodiment, the pillar array (120) is fabricated from $SiO_2$ with a 200 nm pitch, 130 nm height, and 70 nm diameter on the substrate (110), formed from silicon. The metallic back-plane (150) is formed from a 40 nm thick layer of gold, deposited on the pillar array structures and substrate using e-beam evaporation along the normal direction. The deposition process forms the metallic discs (130) in gold on top of each $SiO_2$ pillar while simultaneously forming the gold nanohole metallic back plane on the surface of the silicon substrate. Each disc has a thickness of 40 nm and diameter about 110 nm. During the evaporation process, with a deposition rate of about 0.4 A/s, the gold atoms diffuse onto the sidewalls (120s) of the $SiO_2$ pillars and congregate into random particles with granule sizes between 10 nm and 30 nm, forming the nanoscale metallic dots (140).

Figure 2A:
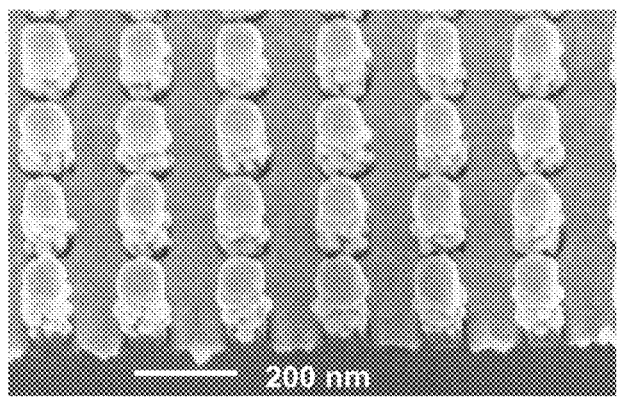
FIGS. 2A and 2B shows a scanning electron micrograph of a Disc-Coupled Dots-on-Pillar Antenna-Array (D2PA) consisting of round $SiO_2$ pillars of 70 nm diameter and 130 nm height on a silicon substrate, the metallic disc, blackplane, and dots of all made of Au with a disc diameter of ~100 nm, a disc and plane thickness of 50 nm, an average dot diameter of 30 nm, and an average gap between the disc and dots as well as between adjacent dots in the range of 0.5 to 15 nm.
Figure 2B:
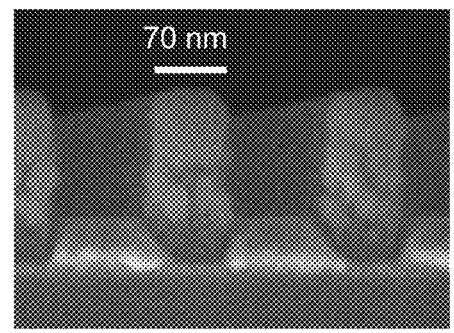

As can be seen in the scanning electron micrographs of FIGS. 2A and 2B, a completed SERS substrate with the gold nanodiscs, random gold nanoparticle metallic dots, and bottom gold nanohole plate (back-plane) are formed in the same evaporation process. The gold nanoparticles scattered on the sidewall (120s) of the $SiO_2$ pillars, forming the nanoscale metallic dots, have narrow gaps of about 0.5 nm-20 nm between them, which are essential to inducing highly enhanced electrical fields. As used herein, the term "gap" is defined as the minimum spacing between the two structures, such as the minimum spacing between two discs (130) or the spacing (140a) between a disc (130) and an adjacent dot structure (140). It also should be pointed out that the even a part of a dot contacts with another dot, an enhancement effects achieved by the present structures still exist, since there are other gaps present between adjacent structures in other locations.

The D2PA structure (100) can enhance light absorption through plasma resonance and nanoantennas. The structure (100) can enhance a local electric field through the nanogaps between the discs (130) and nanodots (140) and the nanogaps (140b) between the nanodots themselves, and assisted by the vertical cavity (for light) formed between the discs (130) and the back plane (150), and the lateral cavity formed by the disc array (120).

More specifically, the structure (100) can enhance the light absorption through the array of nanopillars (120), and can enhance the reflection of an optical signal from the surface through these structures. It may have an enhanced vertical cavity light absorption effect, formed by the discs (130) through the dots (140) and the back plane (150) to enhance the light absorption. It also can have a lateral cavity light absorption effect through the back plane (150) of the metal to enhance the light absorption. It will be recognized by those skilled in the art that any particular D2PA structure (100) may have one, several, or all of these functions, depending upon the specific configuration of the structure 100, including the spacing in the pillar array (120), size of the pillars, size of the discs (130), size of the dots (140), and materials employed.

The enhancement of optical signals by the structure (100) will be a product of enhancement from the nanogaps between features of the structure (100), from plasmon resonance, from antenna absorptions, from antenna radiations, from vertical cavities, as well as lateral cavities. The elements and functions of D2PA structure (100) may be viewed from a different angle. The discs (130) and the spacing gap between the disc and the adjacent metallic dots (140), as well as and between the dots themselves, can affect the local electric field enhancement provided by the structure (100). The dot position and number of dots on each pillar (120) can also enhance the local electric field. The diameter of each pillar and diameter of the capping disc (130) can affect the surface plasmon resident frequency. The silicon dioxide pillar height can affect the cavity length and number of nanogaps, and also can affect the coupling of the disc and the gold back planes. The number of pillars per unit cell can affect the active areas, and the pitch (spacing) in the array of pillars can affect coherent absorption and radiation of light. The gold back plane can affect the antenna and cavity, and the pillar shape can determine the light dependent absorption.

On one example, to achieve a larger SERS EM enhancement factor, it is necessary to: (a) tune the antenna's plasmon resonant frequency of the structure (100) close the middle between a laser excitation frequency ($\omega$) and Raman-shift frequency ($\omega+\Delta\omega$); (b) make the gap between two metal structures as small as possible; (c) enlarge the active area; and (d) have other vertical and/or lateral cavities to further increase light absorption. This can be expressed as:

TOTAL EF (enhancement factor)=(EF due to Plasmon resonance)×(EF due to antenna re-radiation)×(EF due to nanogap)×(EF due to vertical cavity)×(EF due to lateral cavity).

Within the structure (100), multiple variables may be "tuned" to enhance the SERS EF. For example, the diameter of the discs (130) and shape of the pillars (120) may be varied to alter the plasmon resonant frequency, the metallic dots (140) will effect local E-field enhancement, as well the disc-to-dot gap, dot position, and dot counts on each pillar (120); the height of the pillars will affect the resonant cavity length and the number of nanogaps present, as well as the coupling effect between the disc and the metallic back plane. The total number of pillars per unit cell on the surface of the structure (100) defines the active areas, and the pillar spacing (pitch) effects coherent absorption and radiation of optical energy. Finally, the metallic back plane material and thickness is related to antenna and cavity effects. Those of ordinary skill in this field will recognize that each of these variable may be altered as require from the exemplary embodiments shown herein to achieve a structure 100 having desired characteristics or "tuning" to achieve specific enhancements, without departing from the scope of the present invention.

Figure 3A:
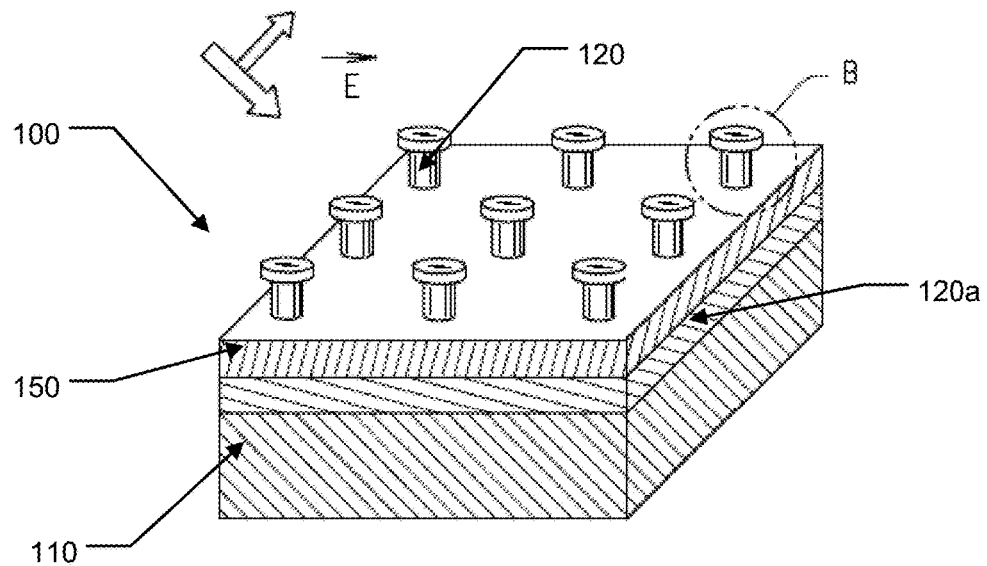
FIG. 3A shows an alternate structure of Disc-Coupled Dots-on-Pillar Antenna-Array (D2PA) with $SiO_2$ under the metal back plane.
Figure 4A:
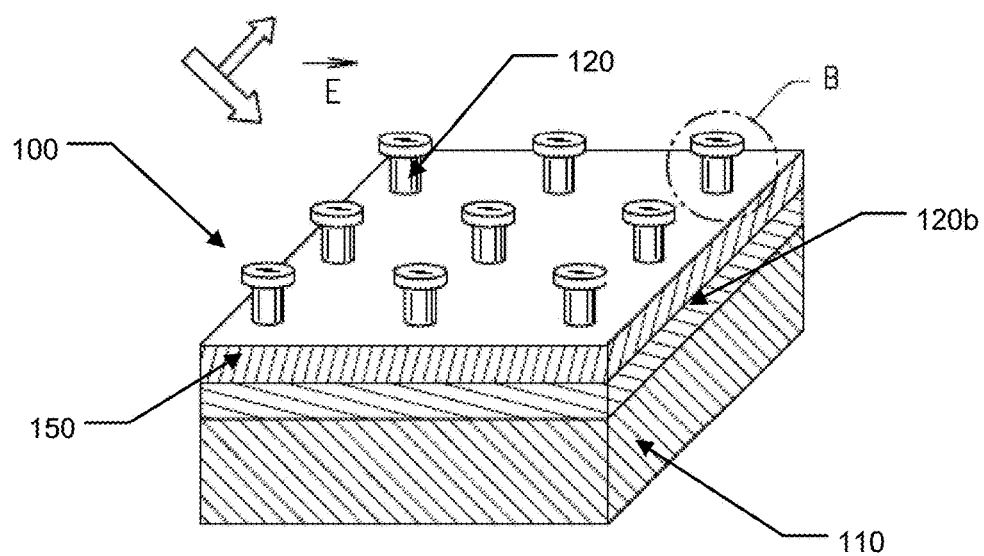
FIG. 4A shows an alternate structure of Disc-Coupled Dots-on-Pillar Antenna-Array (D2PA) having a metallic back plane without holes.
Figure 3B:
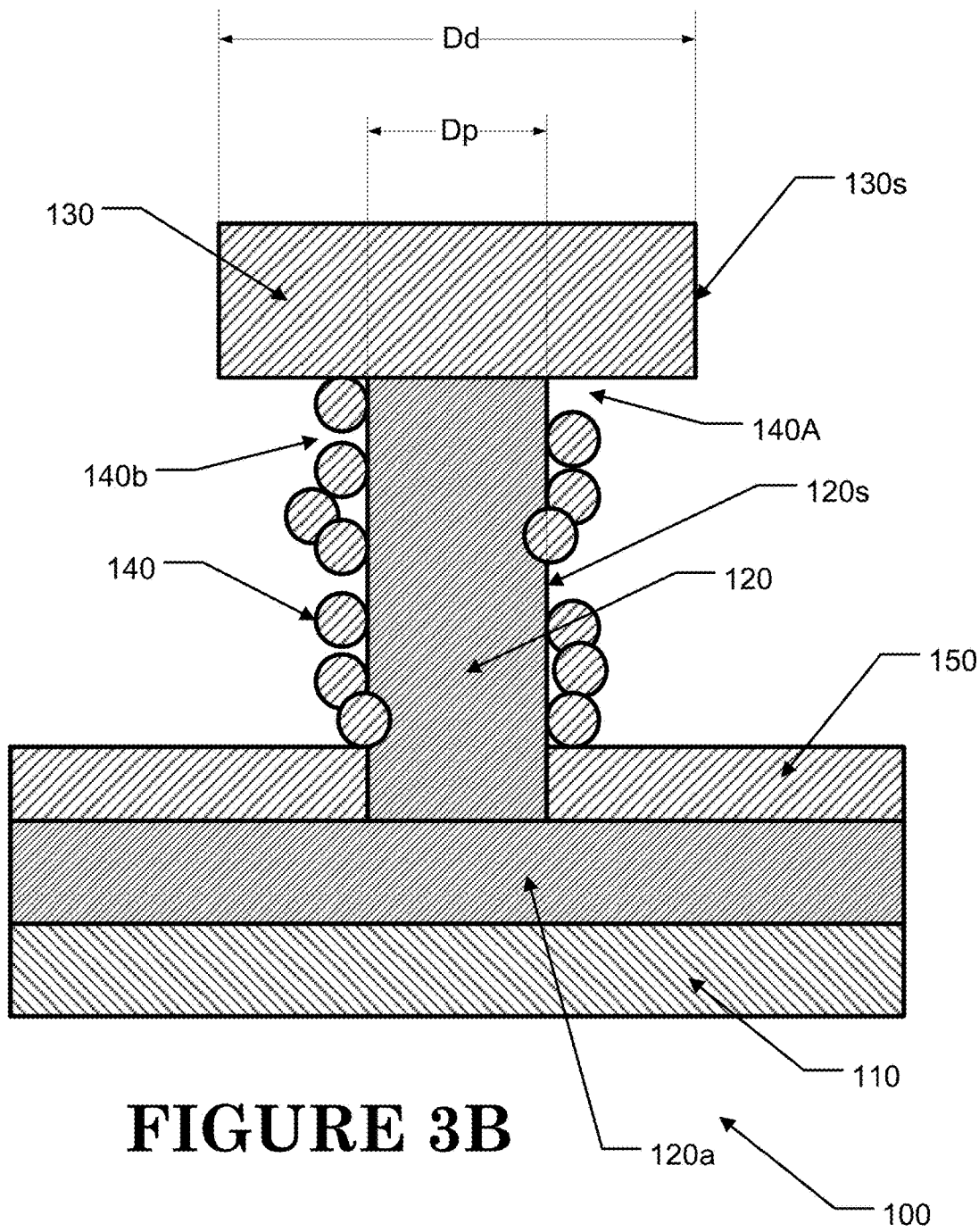
FIG. 3B is a cross-sectional view of a pillar of FIG. 3A.
Figure 4B:
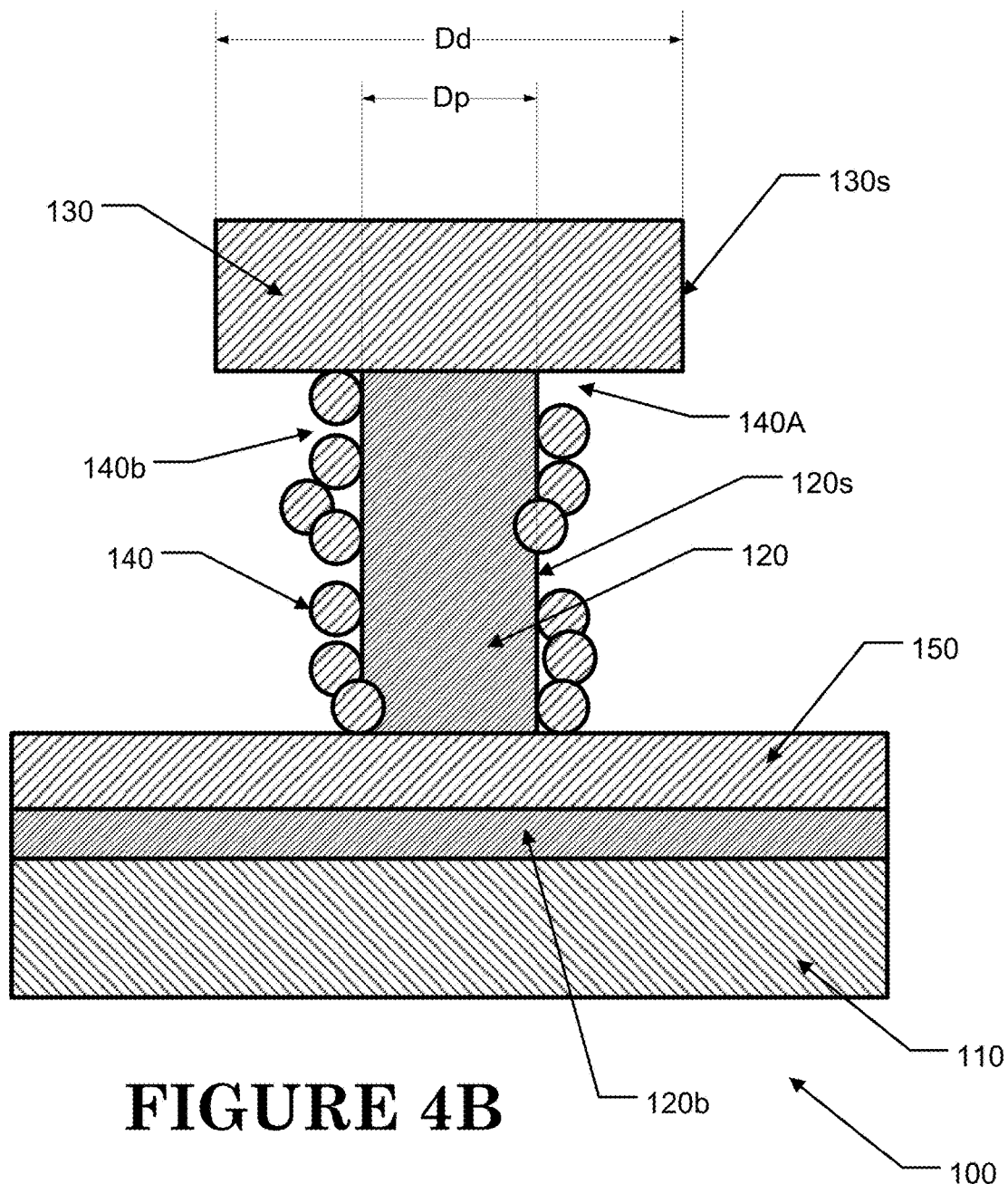
FIG. 4B is a cross-sectional view of a pillar of FIG. 4A.

A variety of configurations for the structure 100 are envisions, for example, FIGS. 3A and 3B illustrate alternate structure of Disc-Coupled Dots-on-Pillar Antenna-Array (D2PA) (100) with a layer (120a) of SiO$_2$ under the metal back plane and which contiguously forms the pillars (120), while FIGS. 4A and 4B illustrate an alternate structure of Disc-Coupled Dots-on-Pillar Antenna-Array (D2PA) having a metallic back plane (150) without holes, such that the pillars (120) are formed directly on the back plane material, which in turn is deposited over a layer (120b) of SiO$_2$ on the underlying substrate (110).

When constructing the D2PA structure (100) of the present disclosure, the material for the underlying substrate (110) can be an insulator, a semiconductors, or a dielectric insulators. The substrate (110) need not be monolithic, but may be of a laminate construction, comprising an insulator or semiconductor material top layer (the layer next to the pillars) while the rest of the substrate is made of any solid material, such as seen in FIGS. 3A and 4A.

The pillars (120) on the top layer of the substrate (110) are preferably formed from an insulating material, but may be semiconductors. Exemplary materials for the formation of the pillars are dielectrics: silicon-dioxide, silicon-nitride, hafnium oxide (HfO), Aluminum oxide (AlO) or semiconductors: silicon, GaAs, and GaN. Once formed, the pillars may have sidewalls (120s) which are columnar (straight), sloped, curved, or any combination thereof. The height of each pillar may be chosen from 5 nm to 7,000 nm, and a lateral dimension of each pillar may be chosen from 5 nm to 8,000 nm. The shape of the top surface of the pillar can be round, a point (of a pyramid), polygon, elliptical, elongated bar, polygon, other similar shapes or combinations thereof. The spacing between the pillars in the array can be periodic or aperiodic. For some applications, a periodic period is preferred and the period is chosen to maximize the light absorption and radiation, which is light wavelength dependent. The spacing (pitch) between adjacent pillars in the array may be from 4 nm to 4000 nm.

Each pillar is topped with a metallic disc (130) which may be formed from either: (a) single element metal, such as gold, silver, copper, aluminum, nickels; (b) a combination of the multiplayer and/or multilayer of the single metals; (c) metallic alloys; (d) semiconductors, (e) any other materials that generate plasmons, or (f) any combination of (a), (b), (c), (d) and (e). The shape of each disc (130) can be a rounded, pointed (as in the form of a pyramid or cone), polygonal, elliptical, elongated bar, polygon, other similar shapes or combinations thereof. The shape of each disc can be the same as, or different from, the shape of the top surface of the associated pillar on which it is disposed. Preferably, a lateral dimension of each disc is from 4 nm to 1500 nm, and a thickness of the disc is from 1 nm to 500 nm. The diameter of the metal discs (130) can be either larger or smaller than the diameter of the supporting pillar (120). The diameter difference can various from 0 to 200 nm depending the working wavelength.

Disposed on the sidewalls (120s) of each pillar (120) between the metallic disc (130) and the metallic back plane (150), the metallic dots (140) have shapes which are approximately spherical, discs-like, polygonal, elongated, other shapes or combinations thereof. The metallic dots on a pillar (120) may all have approximately the same shape, or may be individually varied. The dimensions of the metallic dots are preferably between 3 nm to 600 nm, and may be different in three dimensions. The exact dimension of the dots may be selected for a specific Plasmon resonance, as well regulated by fabrication convenience and the fabrication of the associated gaps (140a, 140b) there between.

Preferably, the gaps (140b) between the neighboring metallic dots (140) and the gap (140a) between the disc (130) and adjacent metallic dots is between 0.5 nm to 200 nm. For many applications, a small gap (140a, 140b) is preferred to enhance the optical signals. The gaps (140a, 140b) may be varied between each metallic dot (140) on a pillar (120).

In the embodiment shown in FIGS. 1A and 1B, the metallic back plane (150) defines a metallic layer on the substrate (110) with a hole for each pillar (120). The thickness of the metallic back plane is selected to be from 1 nm to 2000 nm, with a thickness in the range of 50 nm-200 nm preferred. The material of the metallic back plane can be selected from the same group as is used to form the metallic disc (130) described above, but for a given D2PA structure (100), the metallic back plane can be formed from either the same or a different material as that used to form the discs.

The above descriptions of the D2PA structure (100) are illustrative of the range of the materials, shapes, and dimensions which may be employed, but are not considered to be exclusive. Other materials, shapes, and dimensions may be used as required to achieve a desired enhancement effect. The exact materials, shapes, and dimensions for each D2PA structure (100) will be determined by particular requirements imposed by the light absorption to be enhanced (wavelength, polarization), the light re-radiation to be enhanced, and/or the local electric field to be enhanced.

Figure 5A:
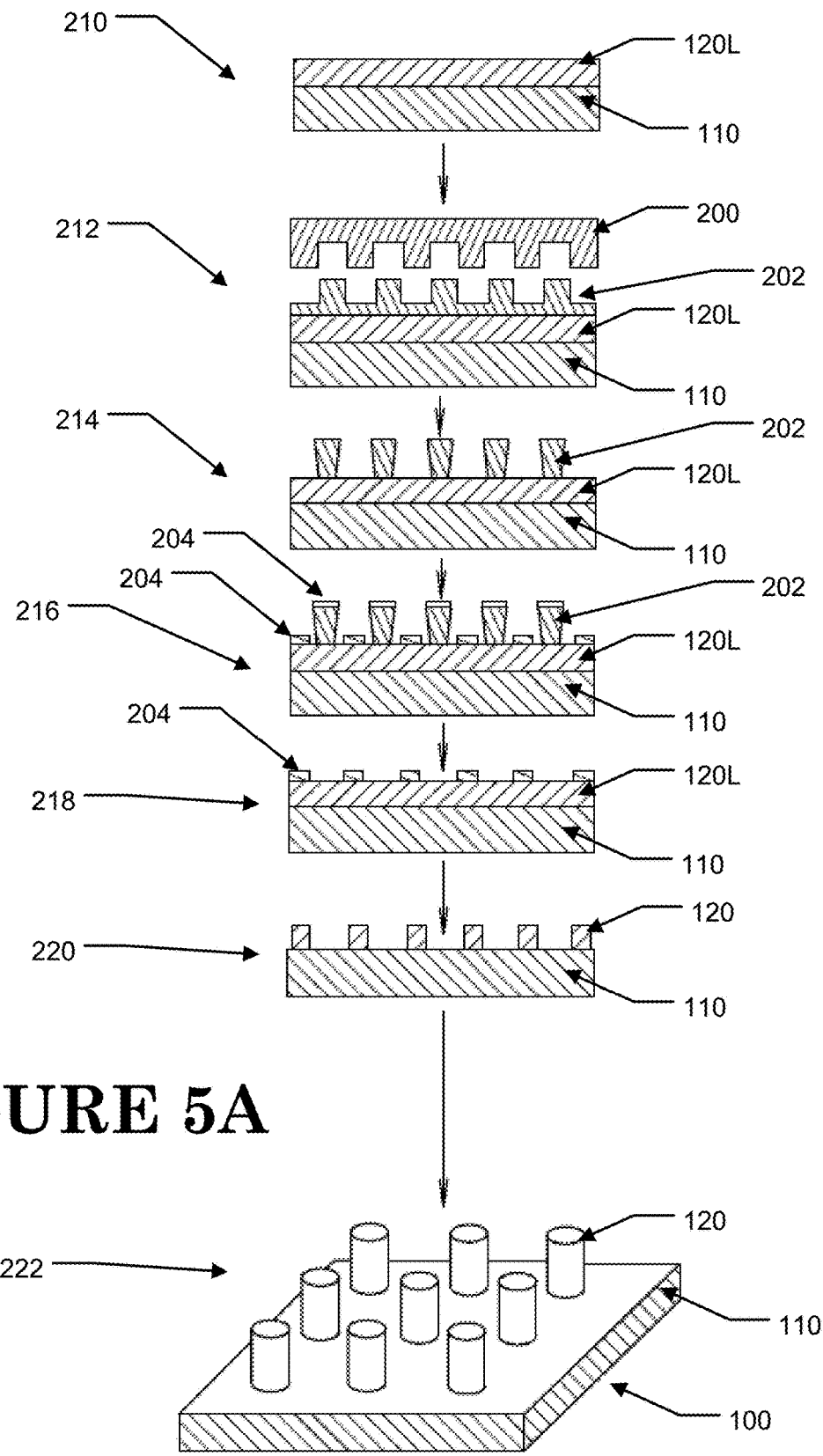
FIG. 5A shows an exemplary fabrication process for creating a pillar array on a substrate using a nanoimprint process.

An exemplary process for the fabrication of a D2PA structure (100) of the present invention is illustrated in FIG. 5. The fabrication process may have several steps as illustrated, and may include other steps incident to lithography and deposition techniques. The initial step (210) is to provide the substrate (110) with a layer of pillar material (120L), such as $SiO_2$. The next step (212) is to employ a lithographic imprinting process to imprint a mold (200) having a pattern of pillars into a resist layer (202) deposited over the layer of pillar material (120L). After imprinting the pattern into the resist layer (202) to create an etch mask, the residual material is removed via an etching process (214) to leave a pattern of pillar-like structures of the resist layer (202). A layer of etch mask material (204), such as chromium (Cr) or other material is then deposited over the pattern of pillar-like structures as seen at (216), and the remaining resist material removed (218), resulting in a pattern of Cr deposited directly on the layer of pillar material (120L). A final etching step (220) which may be a dry etching such as retro-etching, or a wet etching process, removes the unprotected portions of pillar material (120L), and leaves an array of pillars (120) disposed on the surface of the substrate (110). Any remaining etch mask material (Cr) is optionally removed by either a dry or wet etching process, and an evaporation process (222) is employed to deposit the metallic back plane material, disc material, and metallic dots onto the structure (100) in a substantially collimated deposition.

Those of ordinary skill will recognize that the various lithography steps (212) can use any variety of known lithography methods, including electron-beam lithography, ion beam lithography, photolithography, or nanoimprint lithography to form the pattern in the resist material. Similarly, it will be recognized that the etching mask material (204) can be metal dielectric or insulators.

The etch mask material (204) can be deposited on the resist layer (202) before or after the lithography step (212) is performed. A liftoff process (218) will typically be used if the etch masking material is deposited after the lithography step. Alternatively, as shown in FIG. 5, if the step of nanoimprint lithography (212) is used to create a resist pattern first, an etch mask material (204) is subsequently deposited into the resulting trenches second (216), and then a liftoff process (218) is performed.

FIG. 5B shows an alternate exemplary fabrication process for making Disc-Coupled Dots-on-Pillar Antenna Array (D2PA), which consists of the steps of: (1) obtaining a substrate; (2) etching the pillar array; (3) depositing a metal layer from the top; and (4) allowing the metal deposited on the pillar tops to form disc, the metal deposited on the pillar foot to form a metal backplane, and the metal deposited on the sidewall to provide self-forming dots structures;

The D2PA structure (100) of the present invention can be used in various applications, including: (a) enhancement of the optical signals in the detections of molecules and other materials on a structure surface, such as fluorescence, photoluminescence and surface enhanced Raman Scattering (SERS); (b) enhancement of collection of light, such as solar cells; and (c) enhancement of radiation such as light emitting diodes or lasers. Examples of specific applications include single molecule detection, non-intrusive study of reaction dynamics, and identification of trace amounts of biological pathogens and dangerous chemical species Through manipulation of the various parameters of the D2PA structure (100), light of various wavelengths from about 100 nm to about 8000 nm may be manipulated.

Several exemplary D2PA structures (100) manufactured in accordance with the present invention will be described.

A D2PA structure (100) and substrate (110) such as shown in FIGS. 1A and 1B is fabricated by depositing a 40-nm-thick gold on a scaffold $SiO_2$ pillar array using e-beam evaporation from normal direction. The scaffold $SiO_2$ pillar array shown in the scanning electron micrographs of FIGS. 2A and 2B is fabricated by nanoimprint lithography and reactive ion etching. To make the pillar mold used in the imprinting, a 200 nm period grating mold is fabricated using the interference pattern from two coherent 351 nm laser beams, and then the 1-D grating patterns are converted into 2-D pillar patterns through double cycles of imprinting with the grating aligned to orthogonal directions and subsequent processing. The pillar mold is imprinted on a silicon substrate (110) with a layer (120L) of 130 nm thick $SiO_2$.

After a series of fabrication steps; including Cr shadow evaporation (216), residual resist etching (218), Cr etching mask deposition and lift-off, and etching (220) through the $SiO_2$ layer, the $SiO_2$ pillar array is fabricated of 200 nm pitch, 130 nm height and 70 nm diameter on the silicon substrate (110). A 40 nm gold layer (150) is deposited on the pillar array structures (120) using e-beam evaporation along the normal direction and creates the gold nanodiscs (130) on top of the $SiO_2$ pillars (120) and the gold nanohole back plate (150) on the surface of the silicon substrate (110) simultaneously. During the evaporation process with a deposition rate of about 0.4 A/s, the gold atoms diffuse on the sidewall of the $SiO_2$ pillars (120) and congregate into random particles with granule sizes between 10 nm and 30 nm, forming the metallic dots (140).

FIGS. 2A and 2B shows a completed SERS substrate (110) with the gold nanodisc (130), random gold nanoparticles (140), and bottom gold nanohole plate (150) formed in the same evaporation process. The gold nanoparticles (140) scattered on the sidewall of the $SiO_2$ pillars (120) have narrow gaps of about 0.5 nm-20 nm between them, which are essential to induce highly enhanced electrical field with the structure (100).

The large-area SERS substrate (110) are diced into small pieces of about 3 mm×3 mm for measurement with a series of BPE ethanol solutions of different concentrations. The BPE was purified by 3 times recrystallizations before dissolution. 0.182 g purified BPE was dissolved in 10 mL ethanol to form 100 mM BPE ethanol solution, which was then stepwise diluted to lower concentrations. 2 uL solutions BPE solution was dropped on SERS samples using an accurate pipette, and then dried naturally in air without blow dry. This treatment enables accurate control of the total molecule numbers deposited on the SERS substrate surface with known concentration, volume and sample area. To calculate the enhancement on the SERS samples, a piece of control sample without Raman enhancement, which has 50 nm aluminum deposited on a flat glass slide by beam evaporation at 0.6 A/s, was also processed in the same way of the SERS samples, to provide a reference. All samples were characterized using confocal Raman microscope system from HORIBA Jobin Yvon with 5 seconds exposure time and 100× long working distance objective lens with N.A. of 0.75. The excitation source was a 785 nm laser which has a spot diameter of about 1 um.

The SERS enhancement factor of a D2PA sample (100) was measured, which has a 100 nm diameter nanodisc antenna, 130 nm pillar height, and 40 nm gold deposition. The 3 mm×3 mm D2PA sample was treated by above procedure with 2 uL BPE solution of 1 nM concentration. Totally 400 points uniformly distributed on each sample were measured for averaging the overall signal to increase the signal to noise ratio. The analytical enhancement factor [ref] is defined as with other measurement conditions kept same. Following this definition, an EF of 5E7 is obtained by comparing the Raman intensity of 1200 $cm^{-1}$ peak on both the D2PA substrate and the reference sample.

Figure 6:
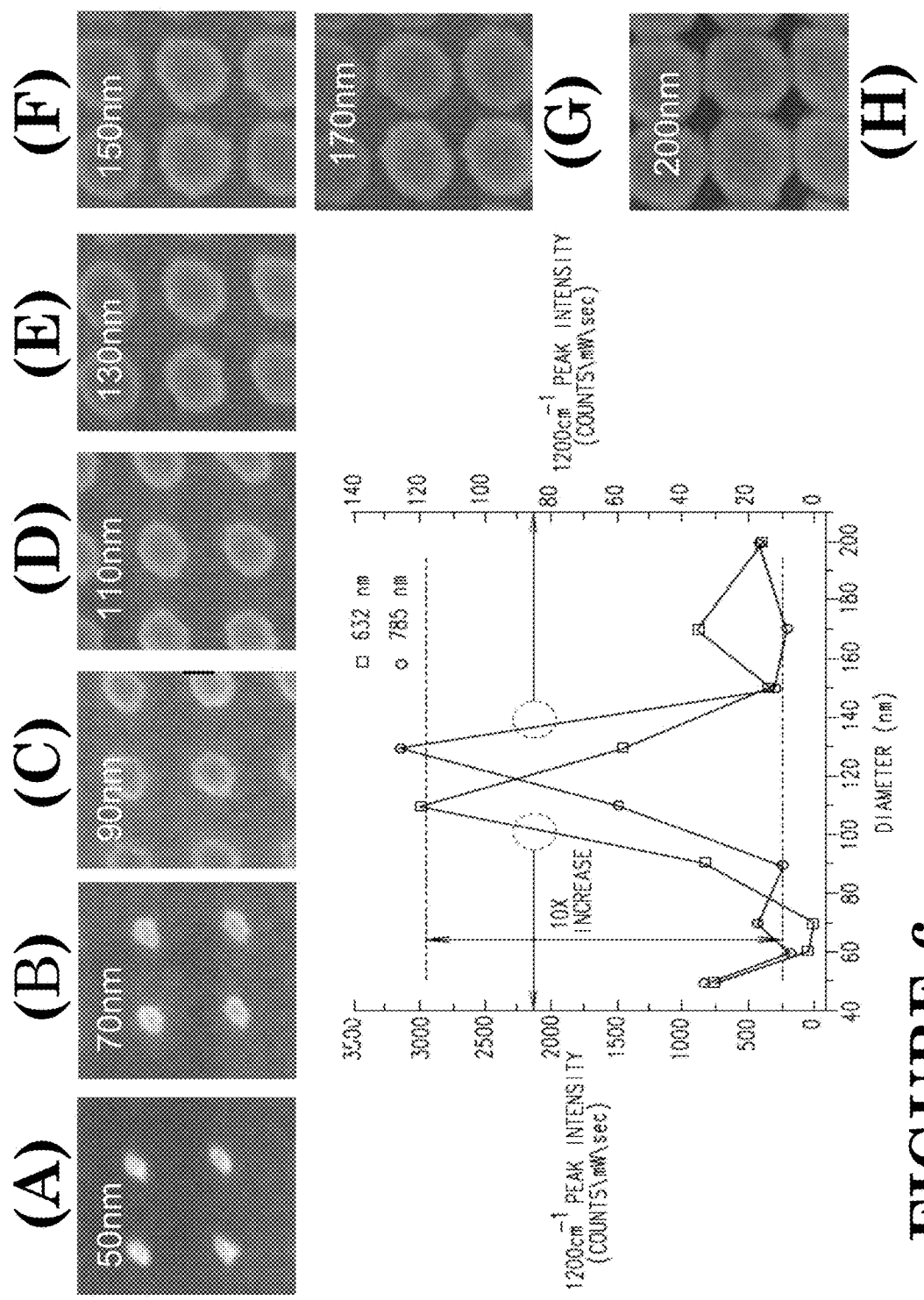
FIG. 6 shows a graph of the effect of the measured D2PA Au Disc Diameter on SERS enhancement of BPE molecules for a variety of disc diameters, shown in the scanning electron micrographs (A)-(H)
Figures 7C, 7D, 7E, 7F, 7G, 7H, 7I, 7J:
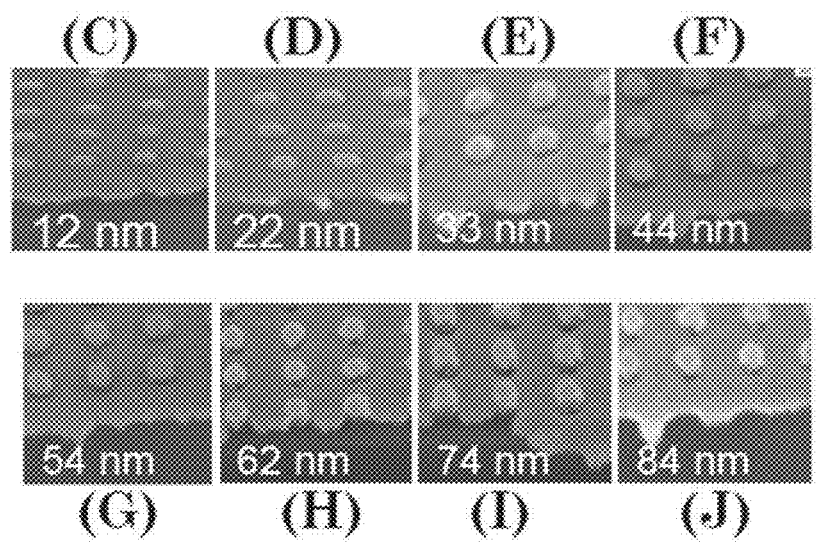
FIGS. 7C-7J are scanning electron micrographs of the various pillar heights charted in FIG. 7A.
Figure 7A:
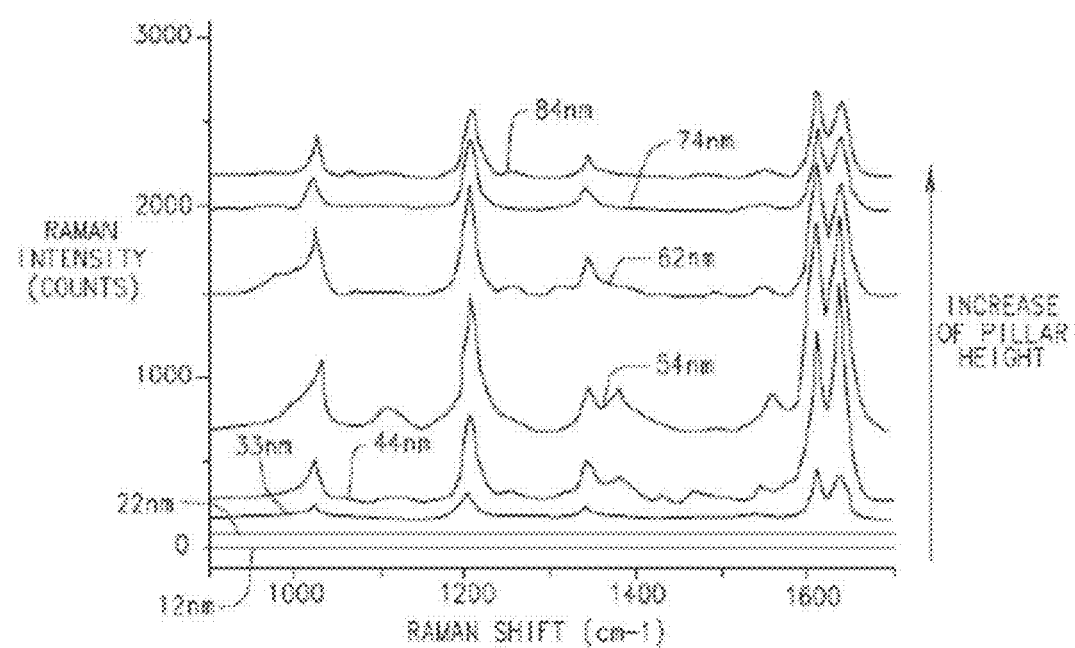
FIG. 7A shows an exemplary graph of the measured SERS signal for D2PA $SiO_2$ Pillar Height with different pillar heights of 33 nm, 44 nm, 54 nm, 62 nm, 74 nm, and 84 nm for BPE molecules, showing the Pillar Height Effect on Raman peak intensity (counts)
Figure 11:
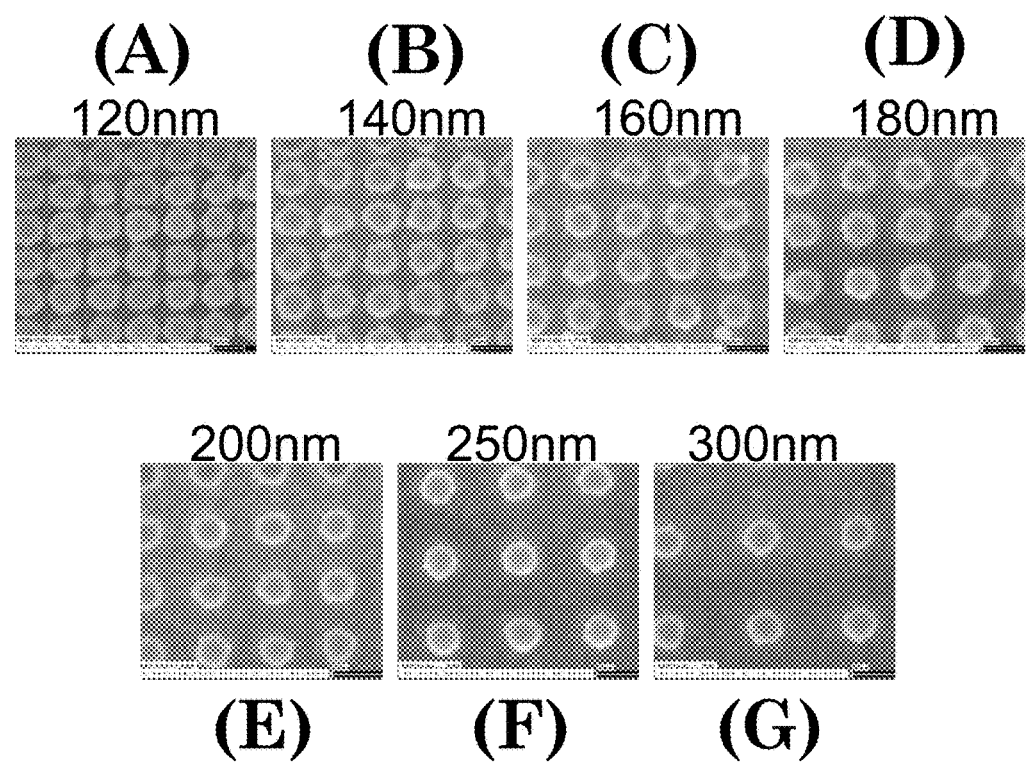
FIG. 11 shows a graph of the effect of the measured Round-Pillar Pitch on SERS enhancement factor for a variety of round-pillar pitch periods, shown in the scanning electron micrographs (A)-(G) (periods=120, 140, 160, 180, 200, 250, and 300 nm)
Figure 11:
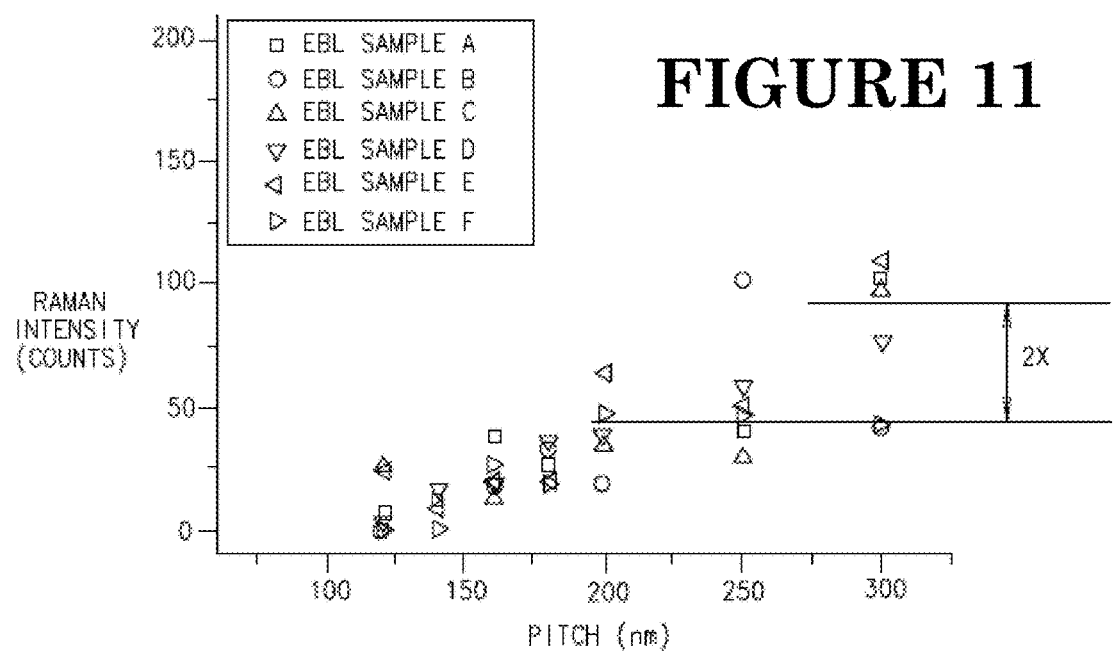
Figure 12:
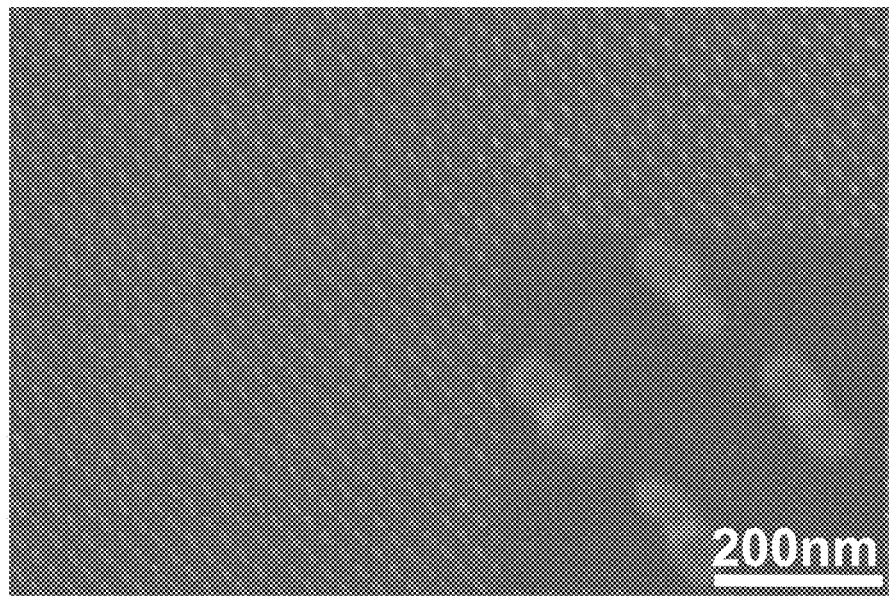
FIG. 12 shows a scanning electron micrographs of an array of single elongated pillars fabricated by nanoimprint.
Figure 13:
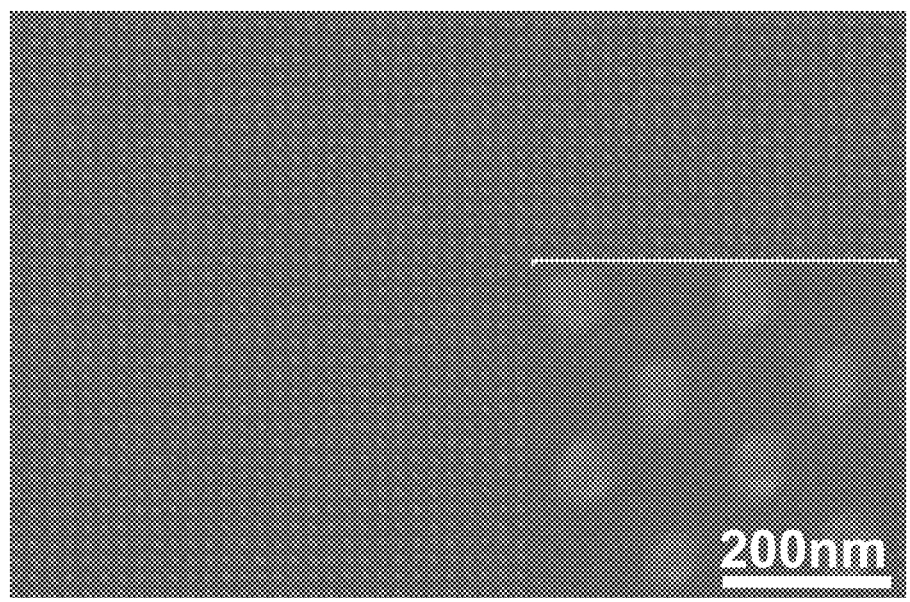
FIG. 13 shows a scanning electron micrographs of an array of double round pillars per unit cell fabricated by nanoimprint.
Figure 15:
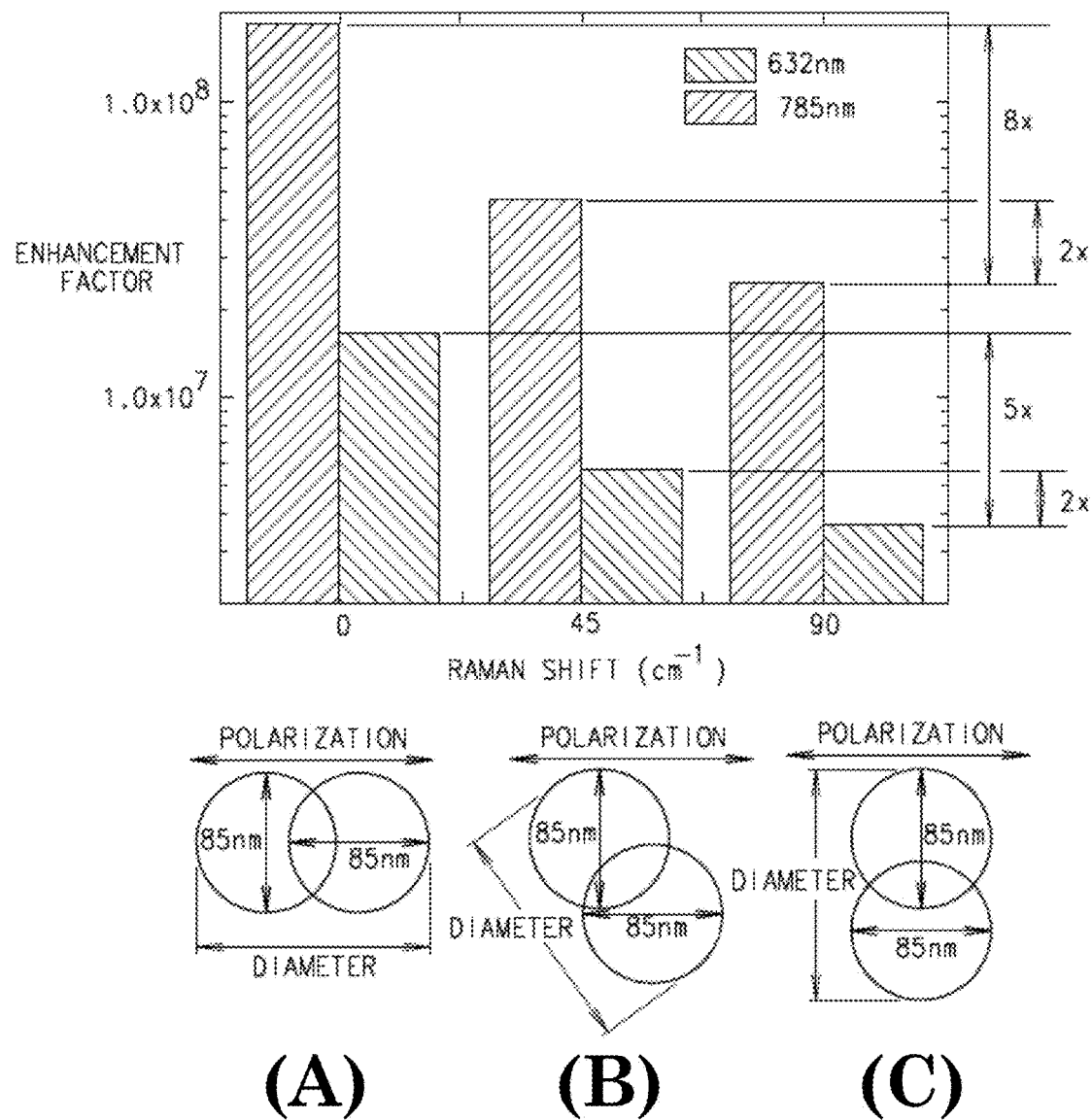
FIG. 15 shows a Light Polarization and Pillar Angle Effect on SERS EF for pillar angles shown in (A)-(C)

The plasmon resonance of the gold nanodisc antenna in the structure plays an important role in enhancing the local electrical field surrounding the pillars and therefore enhancing the overall Raman signal intensity. Under quasi-electrostatic approximation, the resonance wavelength of the subwavelength nanodisc antenna is determined by its geometry which can be altered by changing the pillar diameter while maintaining a fixed gold deposition thickness. To study the effect nanodisc diameter on the SERS EF, a series of D2PA SERS substrates was fabricated with different diameters using e-beam lithography. Each array has a fixed pitch of 200 nm and an etched depth of 130 nm, which are both same as our nanoimprinted D2PA SERS substrate. The diameters of the EBL written D2PA structures range from 50 nm to 190 nm after gold deposition and the array area is 20 um×20 um which is large enough for confocal Raman characterization. The EBL written D2PA structure was processed exactly same as the nanoimprinted D2PA samples, i.e., it was etched using fluorine based RIE and 40 nm gold was evaporated on the whole structure from normal direction. After the EBL patterned substrate was diced in to 3 mm×3 mm square pieces, 2 uL BPE solution of 1 uM concentration was dropped on a single piece containing all the patterns of different diameters. After the SPE molecules were deposited on sample surface by naturally drying the solvent, the sample was subsequently characterized under HORISA ARAMIS Raman Microscope using 632 nm and 785 nm laser excitation respectively. The intensity of the 1200 $cm^{-1}$ peak was measured from arrays of different nanodisc diameters, and plotted and the results are shown in FIG. 6.

At 632 nm excitation, strongest enhancement was observed for 110 nm diameter D2PA structures while this optimal diameter shifted to 130 nm at 785 nm excitation. This result is reasonable since larger nanodisc diameter, therefore larger aspect ratio at fixed thickness, will red shift the nanodisc antenna's resonance wavelength, resulting in a larger optimal diameter at 785 nm excitation than at 632 nm.

Poor reproducibility has been the major hurdle of application of SERS as a regular chemical analysis tool. Since SERS signal strongly depends on nanometer scale features which intrinsically suffer from randomness under current fabrication techniques, it is challenging to reduce both sample-to-sample and spot-to-spot (within same sample) variation. Lithographically fabricated SERS substrates have the advantages of reduced sample-to-sample variation compared with self-assembled or colloidal-based SERS substrates, which should be attributed to a number of high fidelity lithography tools with nanometer scale accuracy, such as nanoimprint lithography. The spot-to-spot variation of SERS signal depends on structure design, especially unit cell (or hot spot) density, and also the laser spot size as larger spot size will generally cause less signal variation by effectively averaging signal from more hot spots. However, in some applications, high uniformity at sub-micron scale, the size of diffraction limited laser spot, is required to achieve high spatial resolution with consistent high enhancement. Considering the subwavelength unit cell and high hot-spot density in each unit cell, our D2PA substrate is expected to demonstrate good uniformity even at smallest laser spot scale.

To characterize the variation of SERS enhancement of the D2PA substrate, one D2PA sample of 3 mm×3 mm size was treated with 2 uL BPE solution of 1 uM and 66 positions were randomly chosen on this sample for Raman mapping. By scanning the excitation laser beam within a certain sample surface, the signal variation may be sampled under different effective excitation spot sizes. The relative standard deviations of the 1200 cm–1 peak intensity may be compared from the 66 measurement points. As a comparison, a commercial Klarite SERS substrate was also diced into 3 mm×3 mm size and measured at 64 randomly chosen positions under different effective laser spot size.

Figure 19:
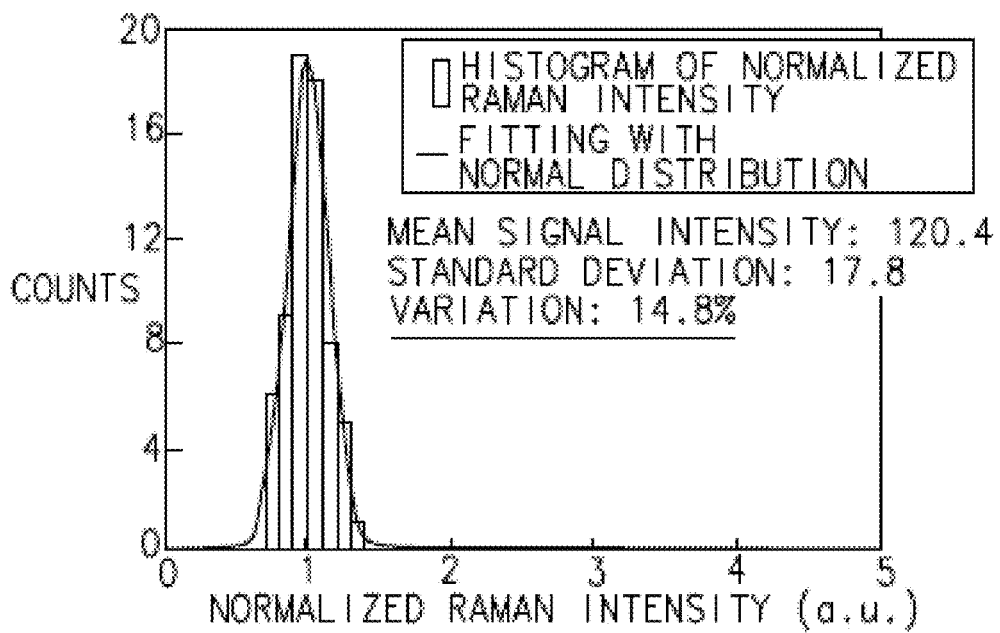
FIG. 19 shows a chart of chart of normalized Raman Intensity (a.u.) versus Counts for a D2PA SERS sample (EF ~$1e^9$) with signal intensity, standard deviation, and variation values.
Figure 20:
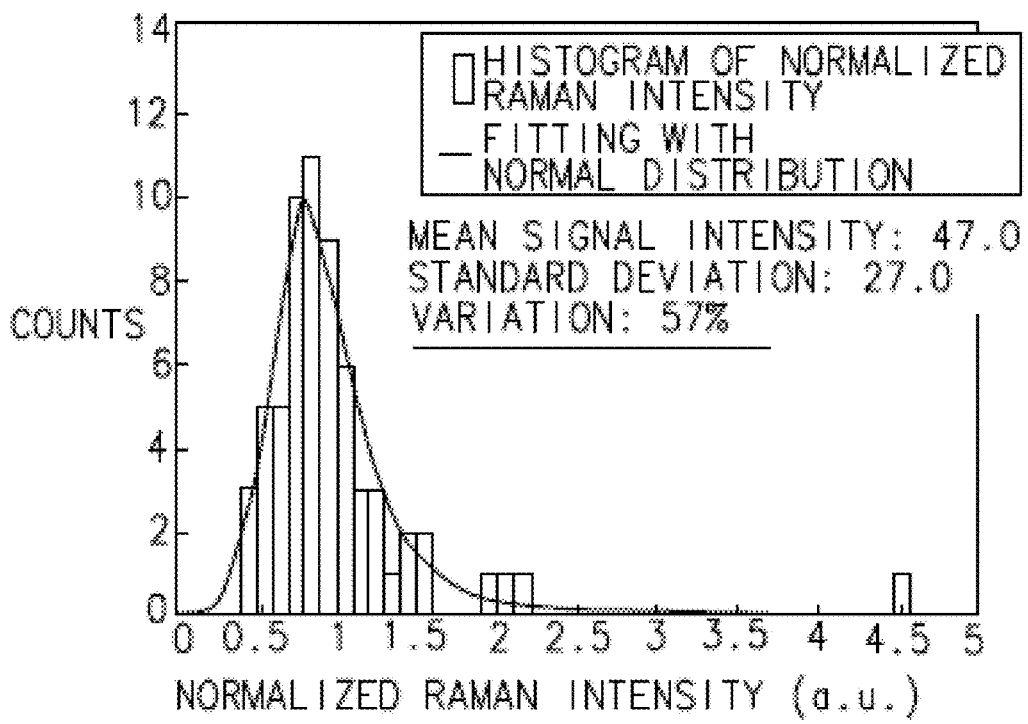
FIG. 20 shows a chart of chart of normalized Raman Intensity (a.u.) versus Counts for a conventional Klarite sample (EF ~$1e^6$) with signal intensity, standard deviation, and variation values.
Figure 21:
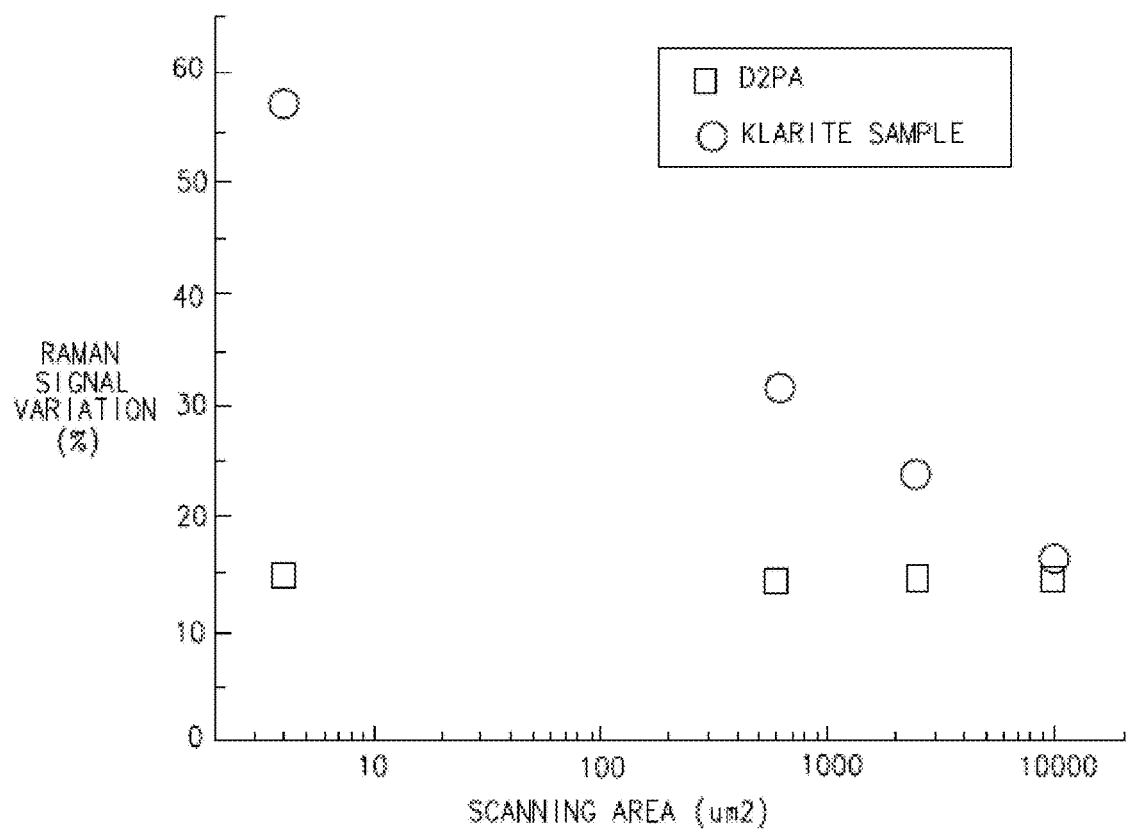
FIG. 21 shows a plot of Raman Signal Variation vs. Scanning Area (D2PA vs Klarite).

FIGS. 19-21 illustrate the results of the spot-to-spot reproducibility of the D2PA sample and the commercial Klarite sample. The histograms in FIGS. 19 and 20 show the signal intensity distribution with a non-scanning laser spot which has a diffraction limited spot size of about 2 um diameter. A 15% relative variation was achieved on our D2PA sample while the Klarite sample shows a 57% variation at 1 um diameter spot size. With increasing effective spot size, in which the excitation laser beam scans within a certain area, Klarite sample exhibits a significantly improved signal variation while the D2PA sample exhibits a consistent variation at below 15%.

These different behaviors of spot-to-spot variation with changing spot size results from the size of the unit cell on each sample. Klarite sample has a unit cell of about 2 um×2 um, which is about 100 times larger than the single pillar unit cell on the D2PA samples. Therefore, the number of unit cells covered by a fixed scanning area on our D2PA sample is 100 times more than on the Klarite sample. Furthermore, in each of the D2PA unit cells, there are a number of narrow gap hot-spots on the pillar sidewall, all these resulting in an improved average effect even with a non-scanning excitation spot size and contributing to the significantly improved reproducibility on our D2PA sample.

Figure 16:
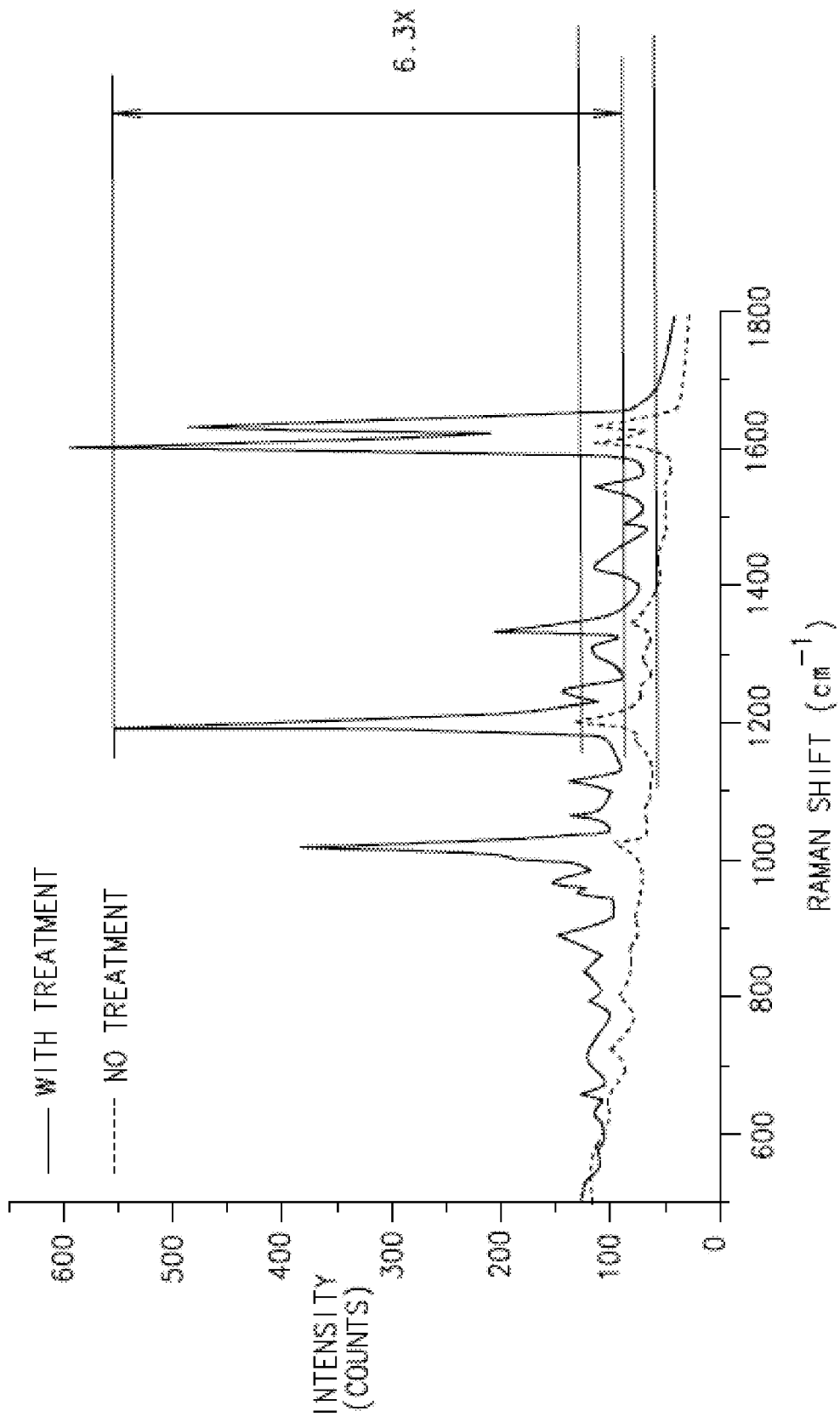
FIG. 16 shows a chart of a measured effect of Chemical Enhancement on D2PA (BPE)
Figure 17:
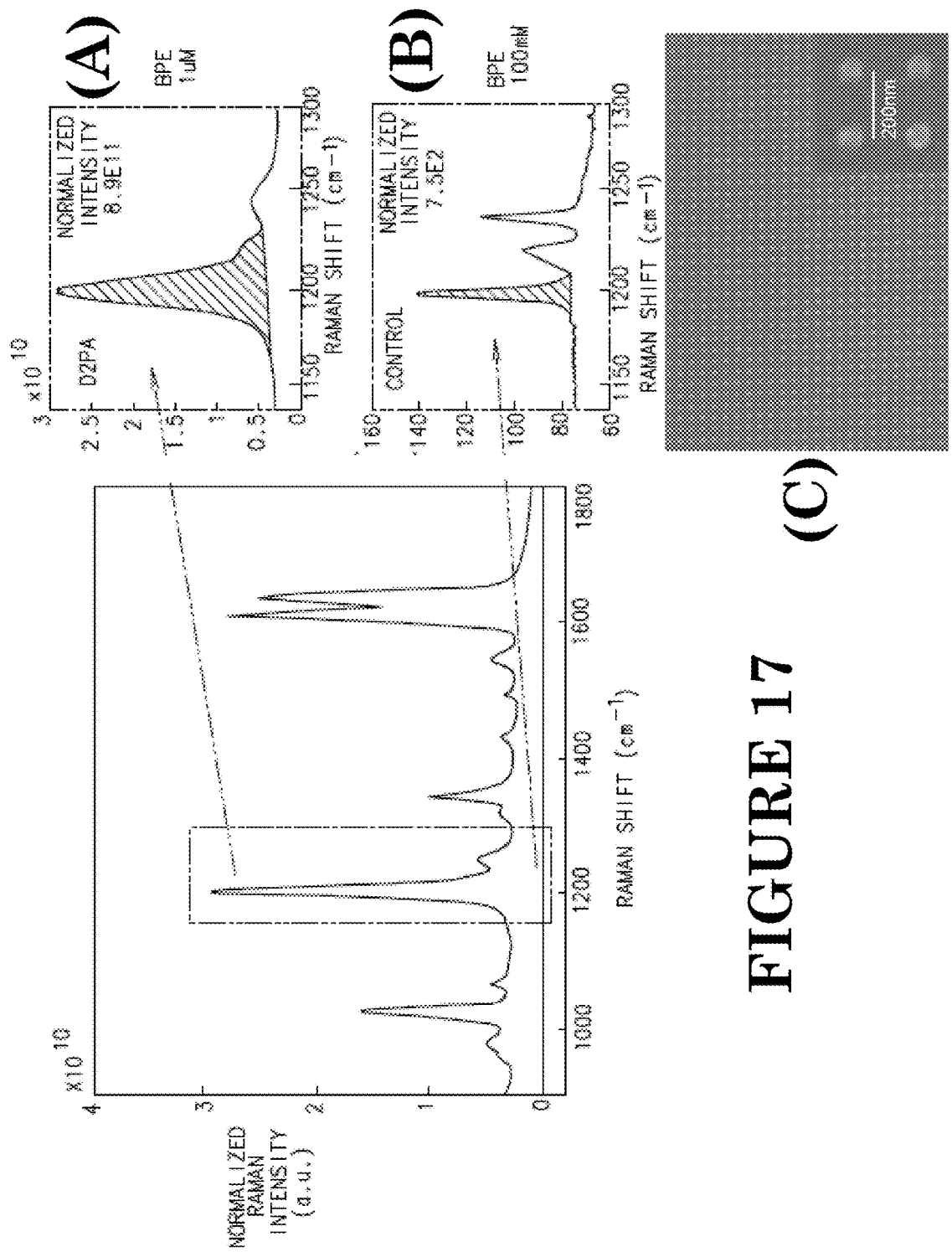
FIG. 17 shows an example of a $1.2e^9$ SERS EF Achieved on D2PA with Round Pillars, illustrating the D2PA sample effect (A) in comparison with the control sample effect (B), and a scanning electron micrograph (C) of the single pillar D2PA utilized.
Figure 18:
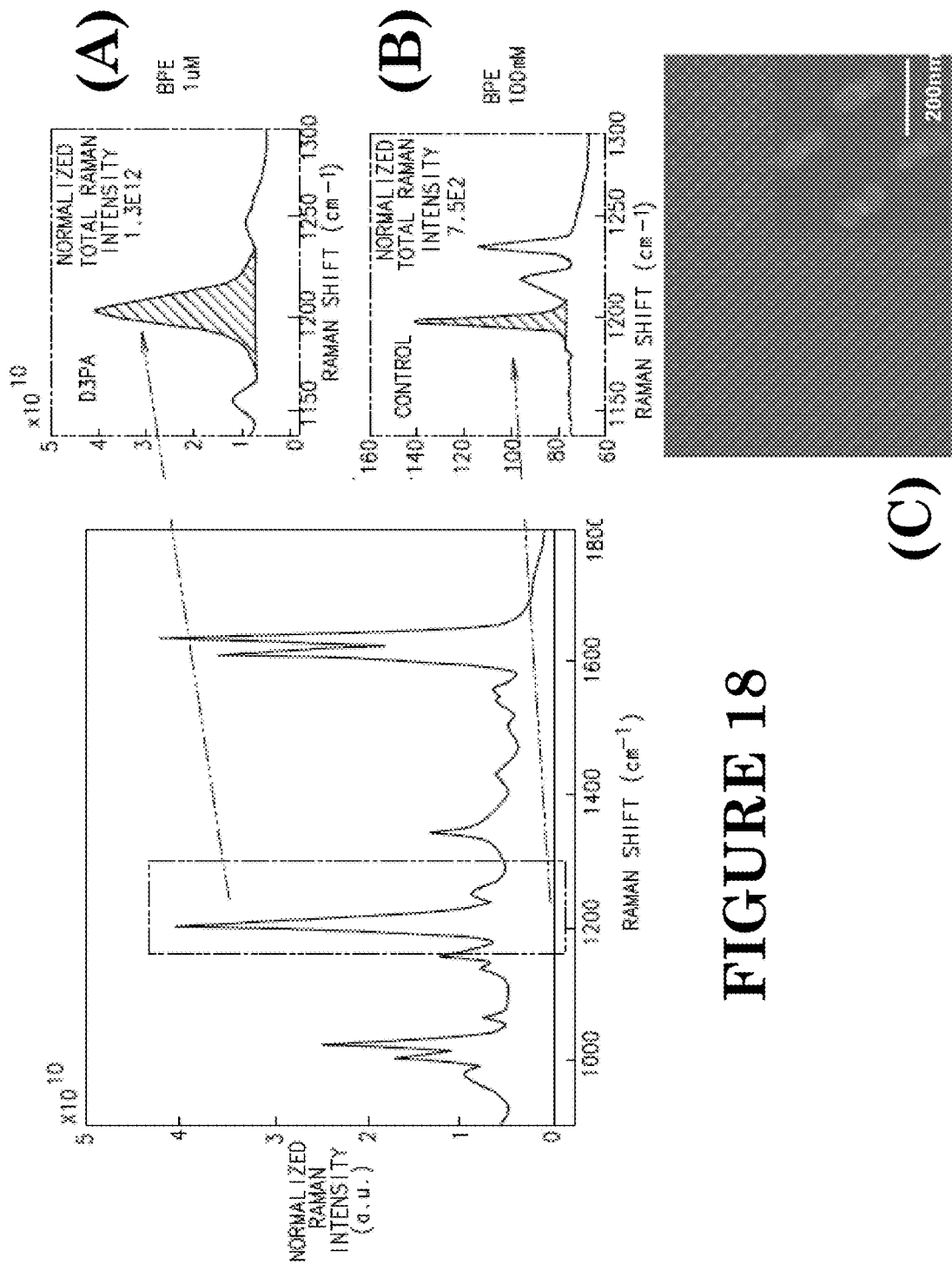
FIG. 18 shows an example of a $1.7e^9$ SERS EF Achieved on D2PA with Elongated Pillars, illustrating the D2PA sample effect (A) in comparison with the control sample effect (B), and a scanning electron micrograph (C) of the single pillar D2PA utilized.

Various other properties of D2PA have been studied experimentally as show in FIGS. 7 to 18. The metallic dots (140), the back plane (150), and all other features of the structures (100) are significant to high signal enhancement. Furthermore with chemical enhancement, the SERS signal was increased by another 6.3× to increate the SERS total enhancement factor to above $1e^9$, as shown in FIG. 16.

It should be pointed out that the structure dimensions presented herein are optimized for an excitation light wavelength of about 780 nm. When working at different light wavelength, it will be recognized that some of the structure dimensions should be scaled with the light wavelength change. For example, when the working wavelength is changed to a longer wavelength, the diameter of the metallic discs (130) should be increased.

To achieve large SERS enhancements, it is necessary to optimize the small gaps (140a, 140b), the sharp edges, the matching of the substrate surface plasmon frequency with the excitation light wavelength, the efficiency for each nano-antennas, the effective coupling between the nanoantenna and the gaps, the vertical and lateral resonant cavity to improve the light absorption, the large number of nanoantenna per unit area, and the large number of SERS effective nanogaps per unit area.

The enhancement structure disclosed herein can be used for the detection of a variety of optical signals of materials and can also improve or alter some other properties of the material. The detection includes fluorescence, SERS, and photoluminescence. The improved optical property can include photo cell absorptions to the light and generate signals.

As various changes could be made in the above constructions without departing from the scope of the disclosure, it is intended that all matter contained in the above description or shown in the accompanying drawings shall be interpreted as illustrative and not in a limiting sense.

In one embodiment, the present invention sets forth a method for enhancing detection of a property, such as an optical property, of a substance, such as a material or a single molecule, utilizing a enhancement structure (100). The method includes the steps of: (1) placing the substance in proximity to the enhancement structure (100); (2) illuminating the substance and/or enhancement structure (100) with light (E); and (3) detecting light from the substance. The enhancement structure (100) consists of a substrate (110); at least one nanoscale pillar (120) extending from a surface of the substrate; a nanoscale metallic disc (130) on top of each pillar; a metallic back plane (150) at a foot of each pillar, said metallic back plane covering a substantial portion of the substrate surface; and at least one nanoscale metallic dot structure (140) on an external vertical surface or sidewall (120s) of each pillar. Alternatively, the substance is disposed on the enhancement structure in said placing step, instead of merely in proximity thereto.

The enhancement structure may be constructed with one or more features specific to the property of the substance which is to be detected. These features include including the material selection, the nanoscale pillar height, the nanoscale pillar sidewall shape, the nanoscale metallic disc shape, the nanoscale metallic dot structure spacing (140a, 140b), the metallic materials, and the metallic backplane configuration. The selection of the nanoscale metallic dot structure spacing further includes selecting a gap distance (140b) between adjacent nanoscale metallic dot structures and/or selecting a gap spacing (140a) between the nanoscale metallic disc and adjacent nanoscale metallic dot structures.

Light detected from the substance in proximity to the enhancement structure may be associated with the detection of molecules or other materials on a surface of the substance, and may, for example, define optical signals such as a fluorescence optical signal, a photoluminescense optical signal, or a Surface Enhances Raman Scattering (SERS) optical signal. The detected light may be generated near the surface of the substance or incoming to the surface of the substance, and typically has a wavelength in the range from 10 nm to 30 microns. Preferably, the detected light has a wavelength which is substantially near a resonant peak wavelength of the nanoscale pillar and nanoscale metallic disc structures of the enhancement structure.

In a second embodiment, the present invention sets forth a nanoscale structure (100) that enhances, at a material, a local electric field induced by incoming light, absorption of light, or the radiation of light generated at the surface of the material. The structure (100) comprises a substrate (110); at least one pillar (120) extending from a surface of the substrate; a metallic (conductive) disc (130) disposed on top of each pillar; a metallic (conductive) back plane (150) at a foot of each pillar covering a substantial portion of the substrate surface; and at least one metallic (conductive) dot structure (140) disposed on an external vertical surface or sidewall (120s) of each pillar.

The substrate (110) of the nanoscale structure may be an electrical insulator, a dielectric insulator or a semiconductor. Optionally the substrate may be a laminate structure, and wherein a layer (120a, 120b) at the surface of the substrate is either an electrical insulator or a semiconductor; and wherein a body of the substrate below the surface layer consists of any solid material.

The pillar (120) of the nanoscale structure may be formed from either an insulator or a semiconductor, and has a top which has a shape selected from the group of shapes consisting of round, pointed, polygonal, pyramidal, elliptical, elongated bar shaped, or any combinations thereof. The sidewall surface (120s) of the pillar may be columnar, sloped, or curved. Preferably, the pillar has a height in the range from 5 nm to 7000 nm and a diameter in the range from 5 nm to 8000 nm. Optionally, the pillar may be part of an array of pillars extending from said surface of the substrate (110), with a spacing between adjacent pillars in the range from 2 nm to 4,000 nm. The array of pillars may define a periodic array with a spacing selected in relation to light of a selected wavelength in order to maximize absorption or radiation of said light using the nanoscale structure. Suitable materials for the formation of the pillars on the nanoscale structure include silicon-dioxide, silicon-nitride, hafnium oxide, aluminum oxide, silicon, gallium arsenide, and gallium nitride.

The metallic discs (130) of the nanoscale structure are formed on top of the pillars (120) from a metal such as gold, silver, copper, aluminum, alloys thereof, or combinations thereof. The surface of the metallic discs need not be uniform, and may have any configuration such as round, pointed, polygonal, elliptical, bar or combinations thereof. Preferably, a lateral dimension of the metallic disc is in the range from 5 nm to 1500 nm and a vertical thickness of said metallic disc is in the range from 1 nm to 500 nm.

The metallic dot structures (140) disposed on the pillar sidewalls (120s) of the nanoscale structure (100) each have a shape selected from a group of shapes consisting of approximately spherical, circular, polygonal, elongated or combinations thereof, and have dimensions in the range 3 nm to 600 nm. A gap (140a) between the metallic dot structures and the metallic disc (130) on a common pillar is in a range from 0.5 nm to 600 nm, as is the gap (140b) between adjacent metallic dot structures (140).

The metallic back plane (150) of the nanoscale structure (100) may be configured either with holes through which the pillars (120) extend from surface of the substrate, or may be substantially continuous, with the pillars disposed there on. Preferably, the metallic back plane (150) has a thickness ranging from 1 nm to 2000 nm, and preferably from 50 nm to 200 nm, and is composed of a metal selected from the group of metals consisting of gold, silver, copper, aluminum, alloys thereof, or combinations thereof. The metallic back plane (150) may be formed from either the same material as, or a different material from, the metallic discs (130).

In use, the nanoscale structure (100) of the present disclosure enhances a characteristic or property of an material, such as a single molecule or specimen, in nearby proximity. The characteristic or property may include a local electric field induced by incoming light, absorption of light, or radiation of light generated at the surface of the material.

These enhanced characteristics may consist of an optical signal associated with the detection of molecules or other materials, such as a fluorescence optical signal, a photoluminescense optical signal, and a Surface Enhances Raman Scattering (SERS) optical signal.

The nanoscale structure (100) of the present disclosure may be utilized in a fluorescence detector for molecules or small samples, in a photoluminescence detector for molecules or small samples, or in a surface enhanced Raman scattering detector for molecules or small samples The nanoscale structure (100) of the present disclosure may be made by a variety of methods. An exemplary method for manufacture of the nanoscale structure (100) for enhancing local electric fields, absorbing light or radiating light comprises the steps of: providing a substrate (110) comprising an outer surface of insulating or semiconductive material; forming on the outer surface an array of pillars (120) having a height in the range 5 nm to 7000 nm and a lateral dimension in the range 5 nm to 8000 nm; applying conductive material (130) to the tops of the pillars and to the underlying substrate; and simultaneously (or subsequently) depositing conductive dot structures (140) on the pillar sidewalls (120s). The array of pillars is formed by a process comprising electron beam lithography, ion-beam lithography, photolithography or nanoimprint lithography.

A nanoimprint lithography process for forming the array of pillars (120) requires applying a moldable imprint resist (202) to the outer surface of the nanoscale structure; imprinting the resist with a mold (200) comprising an array of raised pillar regions, forming an array of holes of reduced thickness in the resist layer; selectively etching away the reduced thickness layer in the holes to expose at the bottom of the holes, outer surface areas of the substrate insulating or semiconductive material; depositing an etch masking material (204) in the holes; removing the resist material (202), leaving an array of etch masked regions (204) corresponding to the array of mold pillar regions; etching the outer surface of insulating or semiconductive material (120) to produce an array of pillar regions corresponding to the array of mold pillar regions; and optionally removing the etch mask material.

The invention claimed is:
1. A nanostructure device, comprising:
   a substrate; and
   one or a plurality of pillars extending from a surface of the substrate, wherein said pillars comprises:
      a metallic disc on top of the pillar;
      a metallic back plane at the foot of the pillar, said metallic back plane covering a substantial portion of said substrate surface near the foot of the pillar; and
      a metallic dot structure disposed on an external vertical surface of the pillar;
   wherein said device comprises a nanogap defined by one or more of (i) said disc and said dot structure, (ii) said disc and said back plane, or (iii) said dot structure and said back plane,
   wherein said disc, pillars, dots, and back-plane forms a three-dimensional plasmon cavity antenna;
   wherein lateral dimension of said disc is in the range of from 4 nm to 8000 nm; and
   and wherein said device enhances an interaction or parameter of light in or near said pillar, or an interaction or parameter of light in or near a material that is placed on or in proximity to said device.
2. The nanostructure device of claim 1, wherein said interaction or parameter of light includes at least one of an electric field induced by incoming light, absorption of incoming light, and the radiation of light generated by said material.
3. The nanostructure device of claim 1, wherein said interaction or parameter of light are related to at least one of fluorescence and photoluminescence.
4. The nanostructure device of claim 1, wherein said device enhances optical signals, and said enhancement is a product of enhancement from (i) said nanogaps, (ii) plasmon resonance, (iii) said antenna absorptions, (iv) said antenna radiations, (v) vertical cavities, and (vi) lateral cavities;
   wherein said vertical cavity is formed between said discs and said back plane, and said lateral cavity is formed by the disc array.
5. The nanostructure device of claim 1, wherein the top of said pillar has a shape selected from the group of shapes consisting of round, polygonal, pyramidal, elliptical, elongated bar shaped, or any combination thereof.
6. The nanostructure device of claim 1, wherein said light has a wavelength in the range from 10 nm to 30 microns.
7. The nanostructure device of claim 1, wherein said device enhances a detection of a property of said material.
8. The nanostructure device of claim 7, wherein said property is a property related to a molecule.
9. The nanostructure device of claim 7, wherein said property includes at least one of a fluorescence optical signal and a photoluminescense optical signal.
10. The nanostructure device of claim 7, wherein said property is a property related to a chemical species.
11. The nanostructure device of claim 1, wherein
   said pillars has height in the range from 5 nm to 7000 nm;
   said metallic disc has and thickness in the range of 1 nm to 500 nm;
   said dot structure has a lateral size from 3 nm to 30 nm;
   said nanogap is in a range from 0.5 nm to 600 nm; and
   said plurality of pillars have a spacing between two nearest neighboring pillars in the range from 2 nm to 4,000 nm.
12. The nanostructure device of claim 1, wherein the diameter of said metallic disc is larger or smaller than of said supporting pillar, and the difference in lateral dimension is in the range from 0 to 200 nm.
13. A method for enhancing detection of a property of a substance, comprising:
   placing the substance in proximity to, or in contact with a nanostructure device comprising:
   a substrate; and
   one or a plurality of pillars extending from a surface of the substrate, wherein said pillars comprises:
      a metallic disc on top of the pillar;
      a metallic back plane at the foot of the pillar, said metallic back plane covering a substantial portion of said substrate surface near the foot of the pillar; and
      a metallic dot structure disposed on an external vertical surface of the pillar; and
   detecting outgoing light radiated from said substance and/or said nanostructure device; and
   wherein said device enhances a detection of an optical property of the substance by enhancing an interaction or parameter of light in or near said pillar, or an interaction or parameter of light in or near said substance.
14. The method of claim 13, wherein said property is an optical property.
15. The method of claim 13, wherein said property includes at least one of a fluorescence optical signal and a photoluminescense optical signal.

16. The method of claim 13, wherein said property is a property related to a molecule.

17. The method of claim 13, wherein said property is a property related to a chemical species.

18. The method of claim 13, wherein said outgoing light has a wavelength in the range from 10 nm to 30 microns.

19. A method for fabricating a nanostructure device, comprising:

obtaining a substrate;

patterning one or a plurality of pillars on a top surface of said substrate;

depositing a metallic material layer of said top surface; and allowing the metallic material deposited on the pillar tops to form a disc, the metallic material deposited on the pillar feet to form a metallic back plane, and the metallic material deposited on the sidewall to self-form (or congregate into) at least one metallic dot structure on the pillar sidewall;

wherein at least one nanogap is formed between any pair of the following metallic elements: said disc, said dot structures, and said back plane; and wherein lateral dimension of said disc is in the range of from 4 nm to 8000 nm.

20. The fabrication method of claim 19, wherein said patterning comprises nanoimprinting.

\* \* \* \* \*